United States Patent
Tsubota et al.

(10) Patent No.: US 8,259,904 B2
(45) Date of Patent: Sep. 4, 2012

(54) RADIOGRAPHIC IMAGE CAPTURING SYSTEM, RADIATION CONVERTER, PROCESSOR, SELECTOR FOR SELECTING RADIATION CONVERTER AND PROCESSOR, PROGRAM, METHOD OF SELECTING RADIATION CONVERTER AND PROCESSOR, AND RADIOGRAPHIC IMAGE CAPTURING METHOD

(75) Inventors: Keiji Tsubota, Minami-ashigara (JP); Naoyuki Nishino, Minami-ashigara (JP); Yutaka Yoshida, Fuchu (JP); Yasunori Ohta, Yokohama (JP); Masato Hattori, Minami-ashigara (JP)

(73) Assignee: Fujifilm Corporation, Tokyo (JP)

( * ) Notice: Subject to any disclaimer, the term of this patent is extended or adjusted under 35 U.S.C. 154(b) by 250 days.

(21) Appl. No.: 12/659,721

(22) Filed: Mar. 18, 2010

(65) Prior Publication Data

US 2010/0239065 A1 Sep. 23, 2010

(30) Foreign Application Priority Data

Mar. 19, 2009 (JP) ................................ 2009-068236
Nov. 30, 2009 (JP) ................................ 2009-271517

(51) Int. Cl.
*H05G 1/58* (2006.01)
(52) U.S. Cl. ....................................... 378/116; 378/98.8
(58) Field of Classification Search ................... 378/62, 378/115, 116, 19, 98.8; 250/370.08, 370.09
See application file for complete search history.

(56) References Cited

FOREIGN PATENT DOCUMENTS

| JP | 2000-105297 | 4/2000 |
|---|---|---|
| JP | 3494683 | 11/2003 |
| JP | 2006-247141 | 9/2006 |

*Primary Examiner* — Courtney Thomas
(74) *Attorney, Agent, or Firm* — Jean C. Edwards, Esq.; Edwards Neils PLLC

(57) ABSTRACT

A radiographic image capturing system comprises a radiation converter for converting radiation that has passed through a subject into a radiographic image, a processor for processing the radiographic image, and a selector for, when a plurality of the radiation converters and/or a plurality of the processors are provided, selecting one radiation converter and one processor that have the most appropriate communication state and associating the selected one radiation converter with the selected one processor.

31 Claims, 15 Drawing Sheets

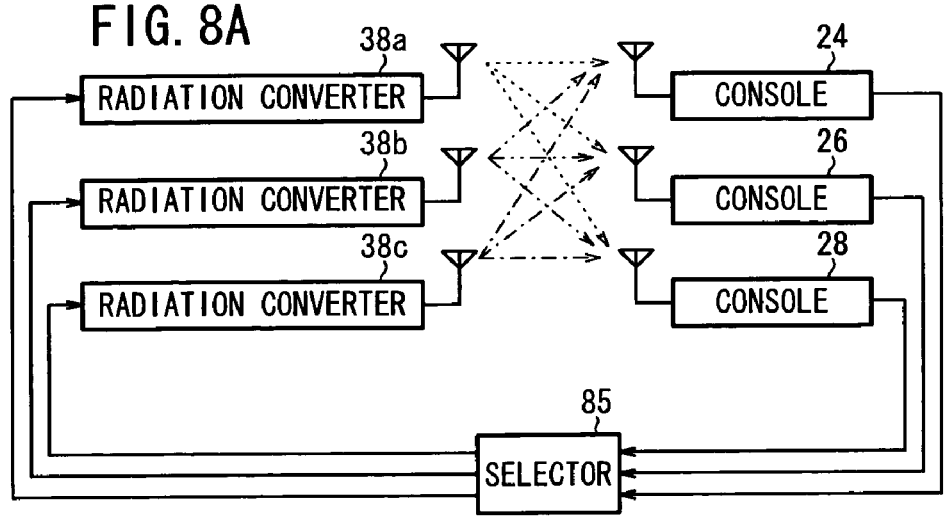
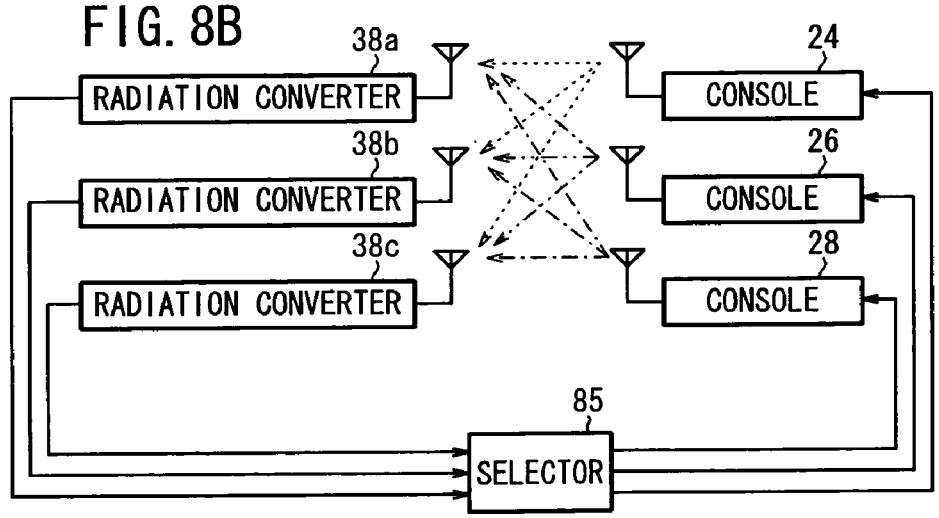

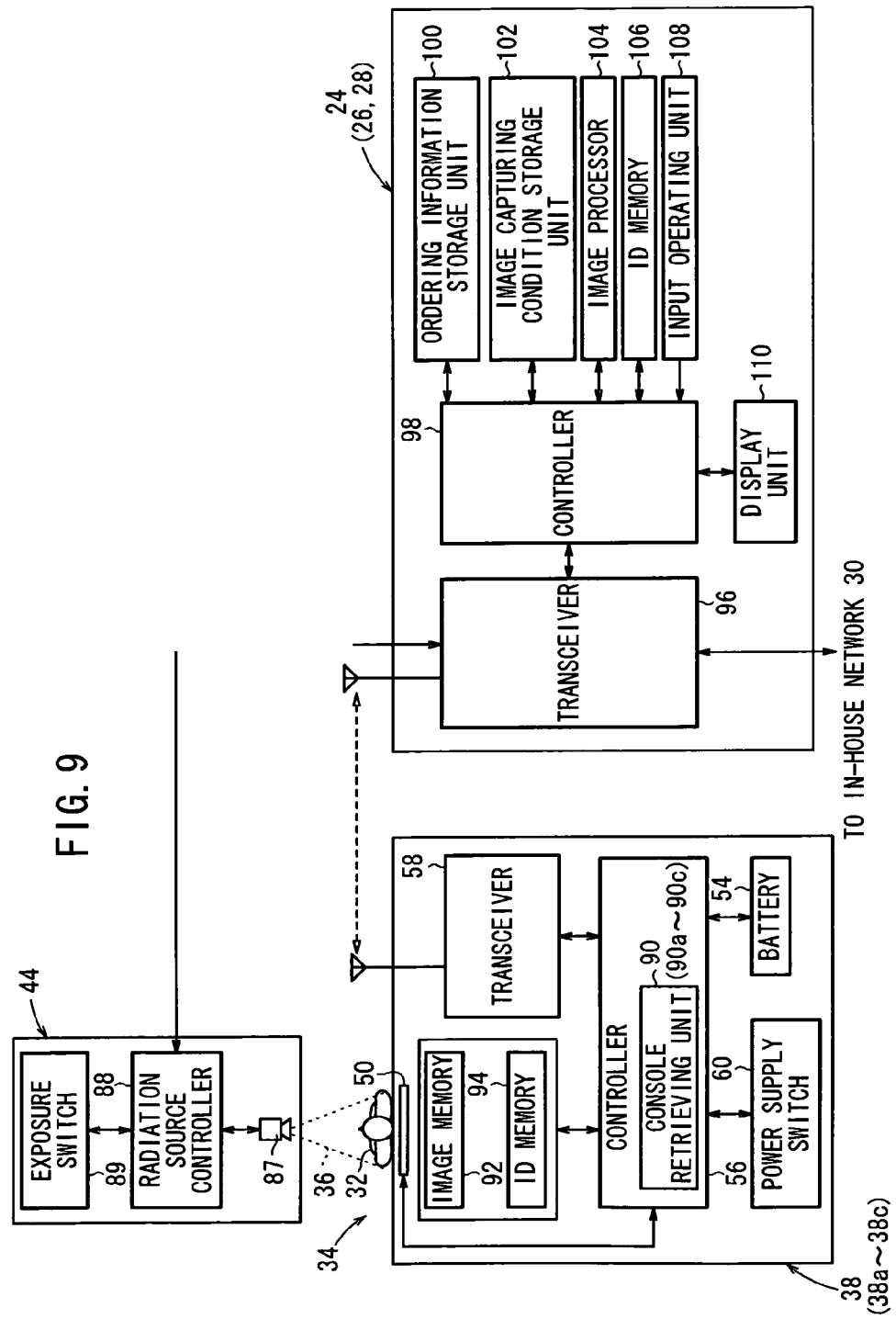

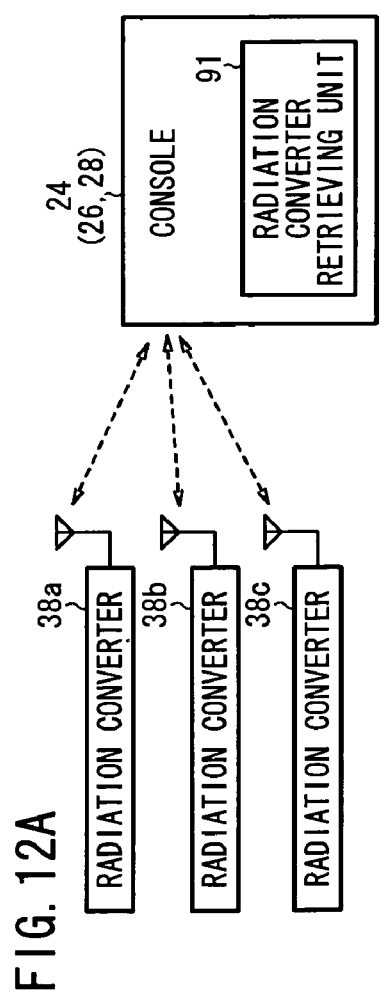
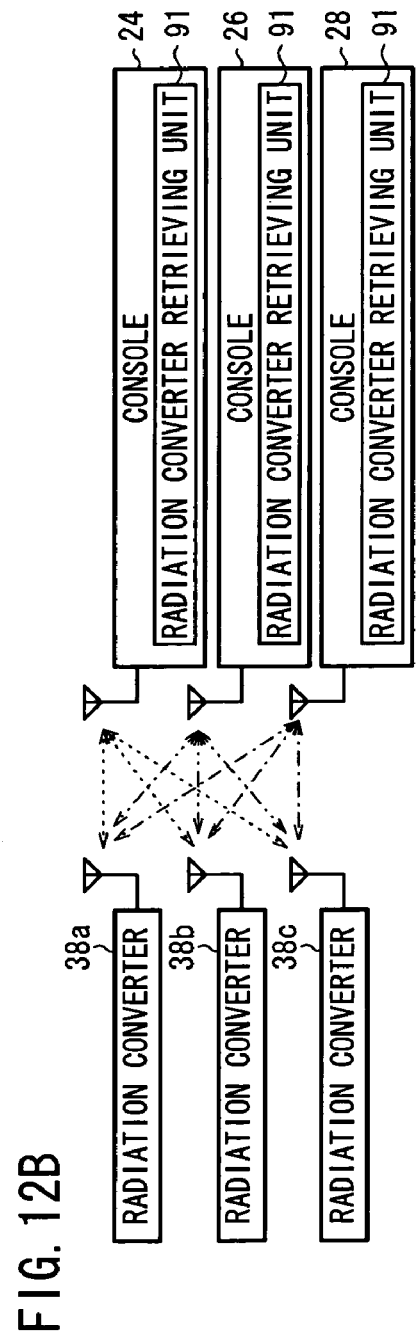

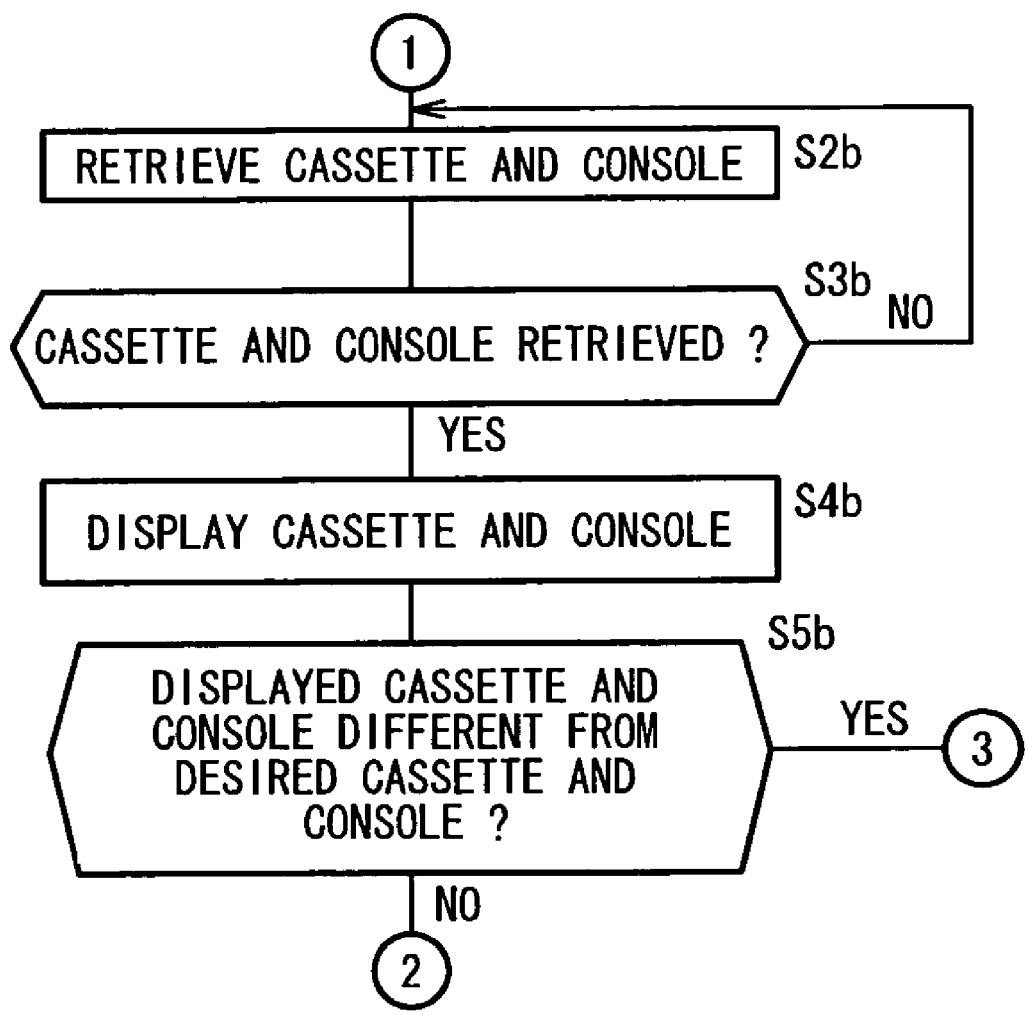

RADIOGRAPHIC IMAGE CAPTURING SYSTEM, RADIATION CONVERTER, PROCESSOR, SELECTOR FOR SELECTING RADIATION CONVERTER AND PROCESSOR, PROGRAM, METHOD OF SELECTING RADIATION CONVERTER AND PROCESSOR, AND RADIOGRAPHIC IMAGE CAPTURING METHOD

CROSS-REFERENCE TO RELATED APPLICATION

This application is based upon and claims the benefit of priority from Japanese Patent Applications No. 2009-068236 filed on Mar. 19, 2009 and No. 2009-271517 filed on Nov. 30, 2009, of which the contents are incorporated herein by reference.

BACKGROUND OF THE INVENTION

1. Field of the Invention

The present invention relates to a selector and a method for selecting one radiation converter and one processor in cases where a plurality of radiation converters and/or a plurality of processors are provided, and relates to a program that is executed by the selector.

Also, the present invention relates to a radiographic image capturing system and a radiographic image capturing method for converting, with a selected radiation converter, radiation that has passed through a subject into a radiographic image, and processing the radiographic image with one processor.

Further, the present invention relates to a radiation converter for selecting one processor from among a plurality of processors, and a processor for selecting one radiation converter from among a plurality of radiation converters.

2. Description of the Related Art

For example, in medical institutions such as a hospital, the following radiographic image capturing system is constructed. In such a radiographic image capturing system, in order to acquire a desired radiographic image of a subject, a doctor uses a radiology information system (RIS) to set subject information including the name, age, gender, etc., of the subject, and image capturing conditions including a radiographic image capturing method, a region to be imaged, an image capturing apparatus to be used, and irradiation conditions for determining a radiation dose at which radiation is applied to the region to be imaged. The above information is supplied to a console (processor) installed in the radiological department. Then, a radiological technician in the site operates the processor to control a specified image capturing apparatus according to the irradiation conditions, thereby acquiring a radiographic image of the subject. The radiographic image is subjected to a predetermined image processing process, and then supplied to a viewer with which the doctor interprets the radiographic image for diagnosis.

In radiological departments of large medical institutions, each image capturing room has the radiation source of such an image capturing apparatus, and such a processor. In this case, the radiological technician brings a radiation converter into a certain image capturing room, and positions the radiation converter at a predetermined position with respect to a subject. Then, the radiation source in the image capturing room radiates radiation to the subject according to image capturing conditions that have been set through the processor. Thus, the radiation converter converts the radiation that has passed through the subject into a radiographic image and sends it to the processor. The processor performs a certain image processing process on the received radiographic image. At this time, unless the radiation converter and the processor are correctly associated with each other, the appropriate radiographic image of the subject can not be acquired.

Japanese Laid-Open Patent Publication 2006-247141 has proposed that a radiological technician performs input operation on the input unit of a processor to select one processor from among a plurality of processors, and associates the selected processor and one radiation converter.

However, in Japanese Laid-Open Patent Publication 2006-247141, the processor is not automatically selected because the radiological technician associates one processor with one radiation converter. Thus, such an associating process by the technician is time-consuming, and the associating process can not be performed efficiently.

Also, even if the one processor and the one radiation converter are associated with each other, it is impossible to transmit/receive the radiographic image stably unless a communication state is secured to such an extent that radiographic images can be transmitted/received between the one processor and the one radiation converter. In this case, the one processor can not acquire the appropriate radiographic image of the subject.

In the above explanation, disadvantages are described, for example, in a case where one processor selected from among the plurality of processors is associated with one radiation converter. However, not only in the above case, but in cases where one radiation converter selected from among a plurality of radiation converters is associated with one processor, and one radiation converter selected from among a plurality of radiation converters is associated with one processor selected from among a plurality of processors, the same disadvantages are expected to occur.

SUMMARY OF THE INVENTION

It is an object of the present invention to perform an association process efficiently by automatically associating one processor with one radiation converter, and to transmit/receive radiographic images by ensuring a good communication state between the processor and the radiation converter.

In order to achieve the above object, the present invention includes the following features.

In one aspect of the present invention, there is provided a selector for selecting a radiation converter and a processor, the radiation converter converting radiation that has passed through a subject into a radiographic image, the processor being capable of processing the radiographic image, wherein when at least a plurality of the radiation converters or a plurality of the processors are provided, the selector selects one radiation converter and one processor that are placed in the most appropriate communication state, and associates the selected one radiation converter with the selected one processor.

In another aspect of the present invention, there is a program for being executed by a selector when at least a plurality of radiation converters or a plurality of processors are provided, the radiation converters converting radiation that has passed through a subject into a radiographic image, the processors being capable of processing the radiographic image, the program comprising the steps of, selecting one radiation converter and one processor that are placed in the most appropriate communication state, and associating the selected one radiation converter with the selected one processor.

In another aspect of the present invention, there is a method of selecting a radiation converter and a processor, the radiation converter converting radiation that has passed through a subject into a radiographic image, the processor being capable of processing the radiographic image, at least a plurality of the radiation converters or a plurality of the processors being provided, the method comprising the steps of, selecting one radiation converter and one processor that are placed in the most appropriate communication state, and associating the selected one radiation converter with the selected one processor.

In another aspect of the present invention, there is a radiographic image capturing system comprising, a radiation converter for converting radiation that has passed through a subject into a radiographic image, a processor for processing the radiographic image, and a selector for, when a plurality of the radiation converters and/or a plurality of the processors are provided, selecting one radiation converter and one processor that are placed in the most appropriate communication state and associating the selected one radiation converter with the selected one processor.

In another aspect of the present invention, there is a radiographic image capturing method comprising the steps of, selecting and associating one radiation converter and one processor by the above method, converting radiation that has passed through a subject into a radiographic image with the selected one radiation converter, sending the converted radiographic image to the one processor, and processing the radiographic image with the one processor.

In another aspect of the present invention, there is a radiation converter for converting radiation that has passed through a subject into a radiographic image, the radiation converter comprising a selector, wherein when a plurality of processors for processing the radiographic image are provided, the selector selects one processor that is placed in the most appropriate communication state, from among the processors, and associates the selected one processor with the radiation converter.

In another aspect of the present invention, there is a processor for processing a radiographic image, the processor comprising a selector, wherein when a plurality of radiation converters for converting radiation that has passed through a subject into the radiographic image are provided, the selector selects one radiation converter that is placed in the most appropriate communication state, from among the radiation converters, and associates the selected one radiation converter with the processor.

In the above aspects of the present invention, a selector or a selecting unit automatically selects one radiation converter and one processor that have the most appropriate communication state, and automatically associates the selected one radiation converter with the selected one processor. Thus, a technician oneself does not need to perform the association process, and the association process can be performed efficiently.

Also, since the one radiation converter and the one processor that have the most appropriate communication state are selected, good communication state is ensured between the one radiation converter and the one processor, thereby to transmit/receive radiographic images stably.

On the other hand, according to the present invention, when a plurality of the radiation converters and a plurality of the processors are provided, a priority order is determined in order of good communication state between the radiation converters and the processors, and the association process is performed based on the determined priority order.

In another aspect of the present invention, there is a selector for selecting a radiation converter and a processor, the radiation converter converting radiation that has passed through a subject into a radiographic image, the processor being capable of processing the radiographic image, wherein when a plurality of the radiation converters and a plurality of the processors are provided, the selector determines a priority order of good communication states between the radiation converters and the processors, and associates the processors with the processors based on the determined priority order.

In another aspect of the present invention, there is a program for being executed by a selector when a plurality of radiation converters and a plurality of processors are provided, the radiation converters converting radiation that has passed through a subject into a radiographic image, the processors being capable of processing the radiographic image, the program comprising the steps of, determining a priority order of good communication states between the radiation converters and the processors, and associating the radiation converters with the processors based on the determined priority order.

In another aspect of the present invention, there is a method of selecting a radiation converter and a processor, the radiation converter converting radiation that has passed through a subject into a radiographic image, the processor being capable of processing the radiographic image, a plurality of the radiation converters and a plurality of the processors being provided, the method comprising the steps of, determining a priority order of good communication states between the radiation converters and the processors, and associating the radiation converters with the processors based on the determined priority order.

In another aspect of the present invention, there is a radiographic image capturing system comprising a plurality of radiation converters for converting radiation that has passed through a subject into a radiographic image, a plurality of processors for processing the radiographic image, and a selector for determining a priority order of good communication states between the radiation converters and the processors, and associating the radiation converters with the processors based on the determined priority order.

In another aspect of the present invention, there is a radiographic image capturing method comprising the steps of associating the radiation converters with the processors based on the above method, converting radiation that has passed through a subject into a radiographic image with the associated one radiation converter, sending the converted radiographic image to the associated one processor, and processing the radiographic image with the one processor.

In another aspect of the present invention, there is a radiation converter for converting radiation that has passed through a subject into a radiographic image, the radiation converter comprising a selector, wherein a plurality of the radiation converters and a plurality of processors for processing the radiographic image are provided, the selector determines a priority order of good communication states between the radiation converters and the processors, and associates the radiation converters with the processors based on the determined priority order.

In another aspect of the present invention, there is a processor for processing a radiographic image, the processor comprising a selector, wherein when a plurality of the processors and a plurality of radiation converters for converting radiation that has passed through a subject into the radiographic image are provided, the selector determines a priority order of good communication states between the radiation converters and the processors, and associates the radiation converters with the processors based on the determined priority order.

In the above aspects of the present invention, a selector or a selecting unit determines a priority order of good communication states between a plurality of the radiation converters and a plurality of the processors, and associates the radiation converters with the processors based on the determined priority order. Thus, a technician oneself does not need to perform the association process, and the association process can be performed efficiently.

Also, since the association process is performed based on the determined priority order of good communication states, good communication state is ensured between each radiation converter and each processor, thereby to transmit/receive radiographic images stably.

The above and other objects, features, and advantages of the present invention will become more apparent from the following description when taken in conjunction with the accompanying drawings in which preferred embodiments of the present invention are shown by way of illustrative example.

BRIEF DESCRIPTION OF THE DRAWINGS

FIGS. 8A and 8B are explanatory diagrams of selecting one radiation converter and one console;

FIG. 9 is a block diagram of another configuration of part of the radiographic image capturing system shown in FIG. 1;

FIG. 12A is an explanatory diagram of selecting one radiation converter;

FIG. 12B is an explanatory diagram of selecting one radiation converter and one console;

FIG. 15 is a flowchart into which the flowchart shown in FIG. 13 is partly modified.

DESCRIPTION OF THE PREFERRED EMBODIMENTS

Figure 1:
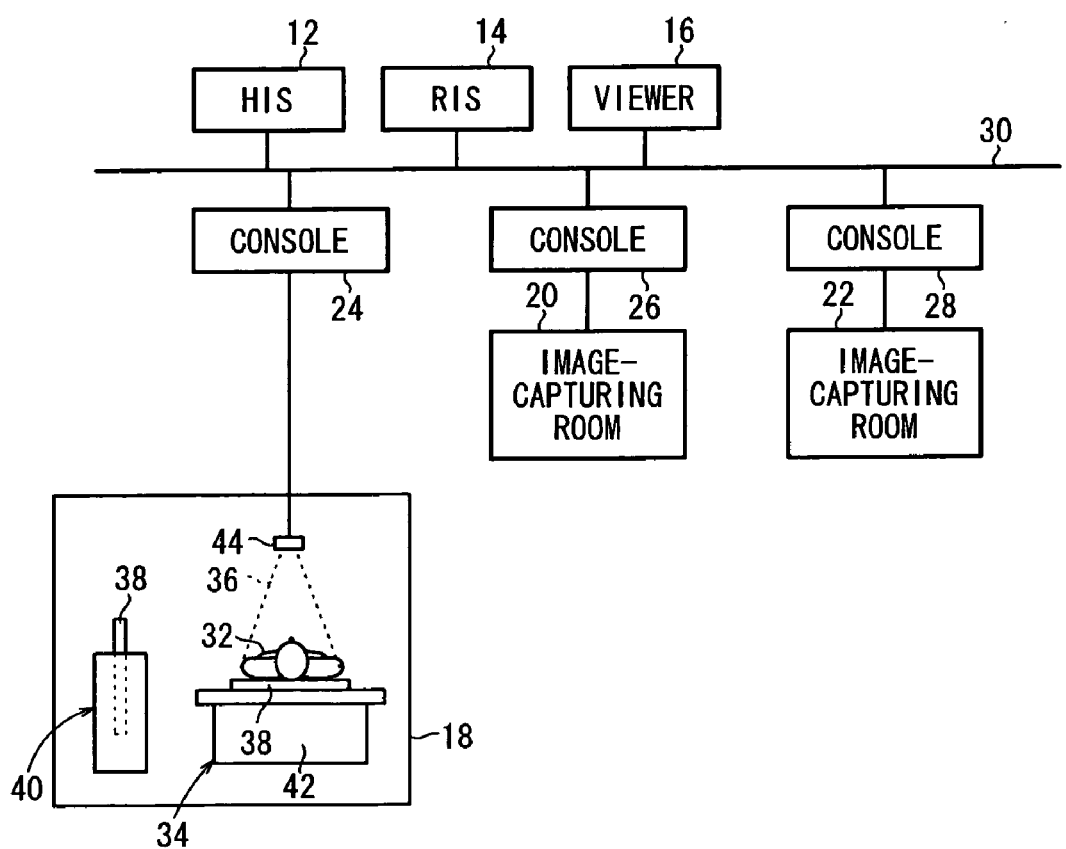
FIG. 1 is a block diagram of a radiographic image capturing system according to an embodiment of the present invention.

Like or corresponding parts are denoted by like or corresponding reference characters throughout views.

FIG. 1 is a block diagram of a radiographic image capturing system 10 according to an embodiment of the present invention.

The radiographic image capturing system 10 comprises a hospital information system (HIS) 12 for managing medical information in a hospital, a radiology information system (RIS) 14 for managing a process of capturing radiographic images in the radiological department of the hospital under the management of the HIS 12, a viewer 16 for allowing a doctor to interpret captured radiographic images for the purpose of diagnosis, and consoles (processors) 24, 26, 28 installed in respective rooms adjacent to a plurality of image capturing rooms 18, 20, 22 in the radiological department. The consoles 24, 26, 28 serve to manage and control image capturing apparatus 34 and radiation converters 38. The HIS 12, the RIS 14, the viewer 16, and the consoles 24, 26, 28 are interconnected by an in-house network 30 in the hospital.

The image capturing room 18 houses therein an image capturing apparatus 34 for capturing radiographic images of a subject 32, typically a patient, while the subject 32 is lying, and a cradle 40 for charging a radiation converter (cassette) 38 for use in the image capturing apparatus 34. The image capturing apparatus 34 comprises an image capturing base 42 and a radiation generator 44 for applying radiation 36 through the subject 32 to the radiation converter 38 which is placed on the image capturing base 42. The other image capturing rooms 20, 22 also house desired image capturing apparatus and cradles therein.

Figure 2:
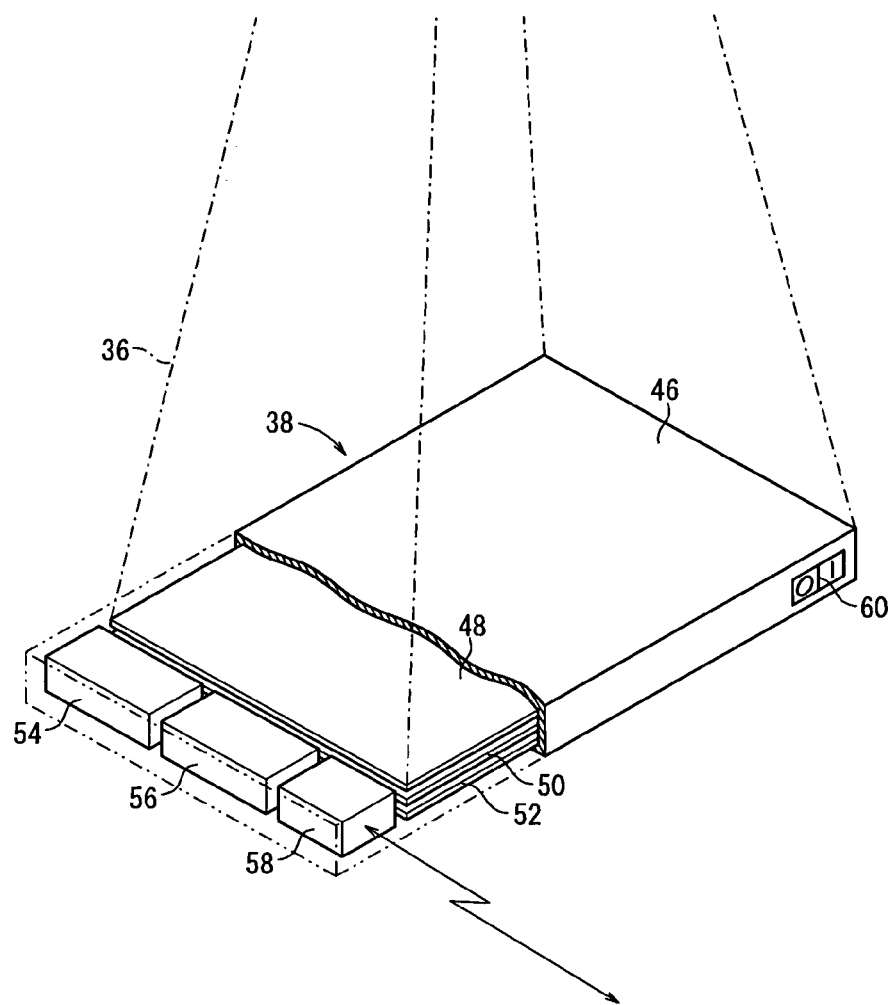
FIG. 2 is a perspective view, partly broken away, of a radiation converter for use in the radiographic image capturing system shown in FIG. 1.

FIG. 2 shows in perspective internal structural details of the radiation converter 38 used in the image capturing apparatus 34.

As shown in FIG. 2, the radiation converter 38 has a casing 46 made of a material permeable to the radiation 36. The casing 46 houses therein a grid 48 for removing scattered rays of the radiation 36 from the subject 32, a radiation conversion panel 50 for detecting the radiation 36 that has passed through the subject 32 and converting the radiation 36 into electric charge information, and a lead plate 52 for absorbing back scattered rays of the radiation 36, which are successively arranged in the order named from a surface of the casing 46 which is irradiated with the radiation 36. The irradiated surface of the casing 46 may be constructed as the grid 48.

The casing 46 also houses therein a battery 54 as a power supply of the radiation converter 38, a controller 56 for energizing the radiation converter 38 with electric power supplied from the battery 54, and a transceiver (first communication unit, wireless transceiver unit) 58 for sending a signal representing a radiographic image of the subject 32 which has been converted by the radiation converter 38 to the console 24 that is connected to the image capturing room 18. The casing 46 has a power supply switch 60 on a side wall thereof for activating the radiation converter 38.

The transceiver 58 and transceivers 96 (see FIG. 4) of the consoles 24, 26, 28 mutually send and receive signals by way of wireless communication using UWB (Ultra Wide Band) or using wireless LAN (Local Area Network).

Figure 3:
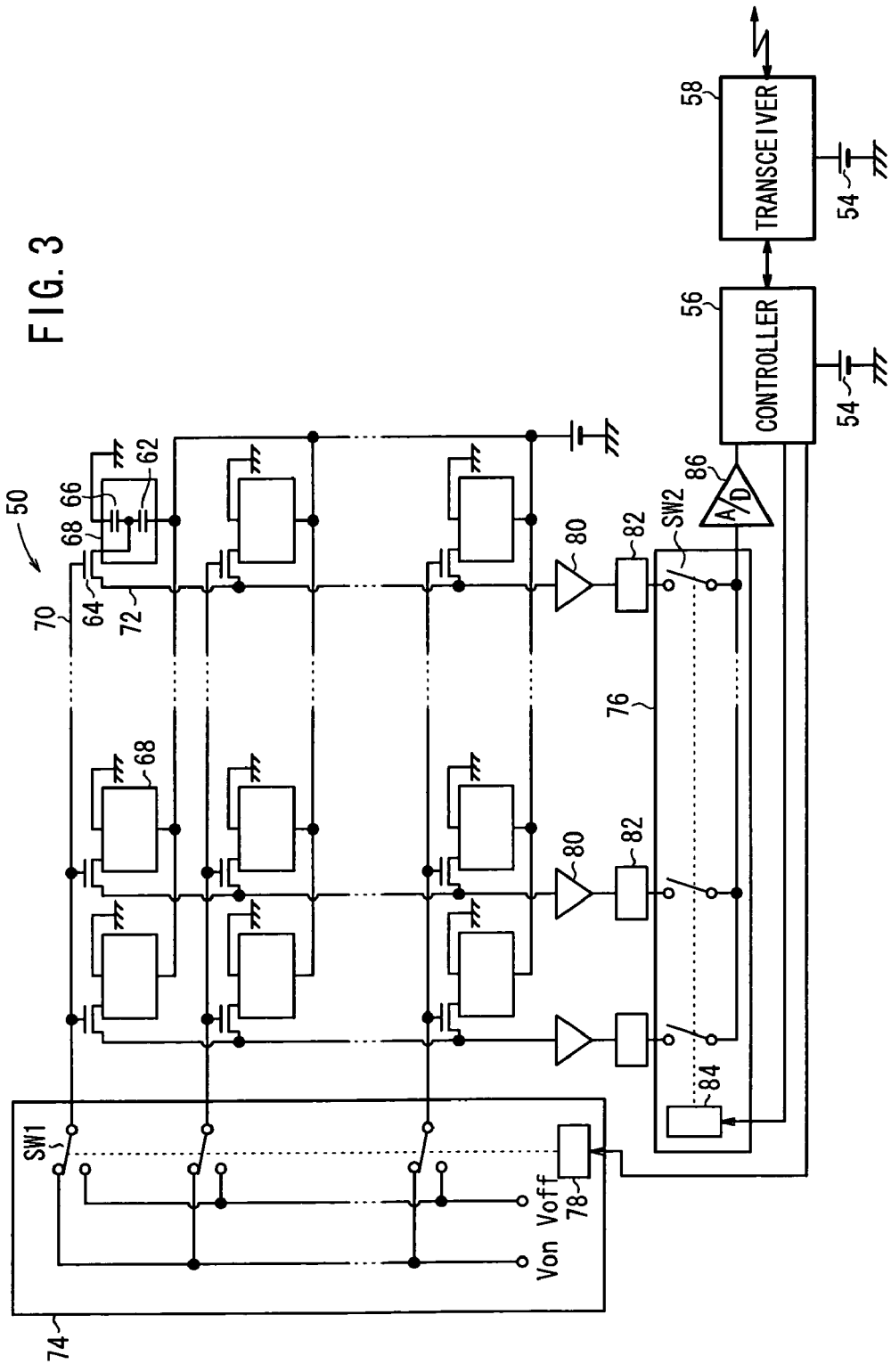
FIG. 3 is a block diagram of a circuit arrangement of a radiation conversion panel in the radiation converter shown in FIG. 2.

FIG. 3 is a circuit arrangement diagram of the radiation conversion panel 50 shown in FIG. 2.

As shown in FIG. 3, the radiation conversion panel 50 comprises an array of thin-film transistors (TFTs) 64 arranged in rows and columns, a photoelectric conversion layer 62 made of a material such as amorphous selenium (a-Se) for generating electric charges upon detection of the radiation 36 (see FIGS. 1 and 2), the photoelectric conversion layer 62 being disposed over the array of TFTs 64, and an array of storage capacitors 66 connected to the photoelectric conversion layer 62. When the radiation 36 is applied to the radiation conversion panel 50, the photoelectric conversion layer 62 generates electric charges, and the storage capacitors 66 store the generated electric charges. Then, the TFTs 64 are turned on along each row at a time to read the electric charges from the storage capacitors 66 as an image signal. In FIG. 3, the photoelectric conversion layer 62 and one of the storage capacitors 66 are shown as a pixel 68, and the pixel 68 is connected to one of the TFTs 64. Details of the other pixels 68 are omitted from illustration. Since amorphous selenium tends to change its structure and lose its function at high temperatures, it needs to be used within a certain temperature range. Therefore, some means for cooling the radiation conversion panel 50 should preferably be provided in the image capturing base 42.

The TFTs 64 connected to the respective pixels 68 are connected to respective gate lines 70 extending parallel to the rows and respective signal lines 72 extending parallel to the columns. The gate lines 70 are connected to a line scanning driver 74, and the signal lines 72 are connected to a multiplexer 76 serving as a reading circuit.

The gate lines 70 are supplied with control signals Von, Voff for turning on and off the TFTs 64 along the rows from the line scanning driver 74. The line scanning driver 74 comprises a plurality of switches SW1 for switching between the gate lines 70 and an address decoder 78 for outputting a selection signal for selecting one of the switches SW1 at a time. The address decoder 78 is supplied with an address signal from a controller 56.

The signal lines 72 are supplied with electric charges stored in the storage capacitors 66 of the pixels 68 through the TFTs 64 arranged in the columns. The electric charges supplied to the signal lines 72 are amplified by amplifiers 80 connected respectively to the signal lines 72. The amplifiers 80 are connected through respective sample and hold circuits 82 to the multiplexer 76. The multiplexer 76 comprises a plurality of switches SW2 for successively switching between the signal lines 72 and an address decoder 84 for outputting a selection signal for selecting one of the switches SW2 at a time. The address decoder 84 is supplied with an address signal from the controller 56. The multiplexer 76 has an output terminal connected to an A/D converter 86. A radiographic image signal generated by the multiplexer 76 based on the electric charges from the sample and hold circuits 82 is converted by the A/D converter 86 into a digital image signal representing radiographic image information, which is supplied to the controller 56. The controller 56 supplies the acquired digital image signal to the console 24 through the transceiver 58 by wireless communications.

The TFTs 64 which function as switching devices may be combined with another image capturing device such as a CMOS (Complementary Metal-Oxide Semiconductor) image sensor or the like. Alternatively, the TFTs 64 may be replaced with a CCD (Charge-Coupled Device) image sensor for shifting and transferring electric charges with shift pulses which correspond to gate signals in the TFTs.

Figure 4:
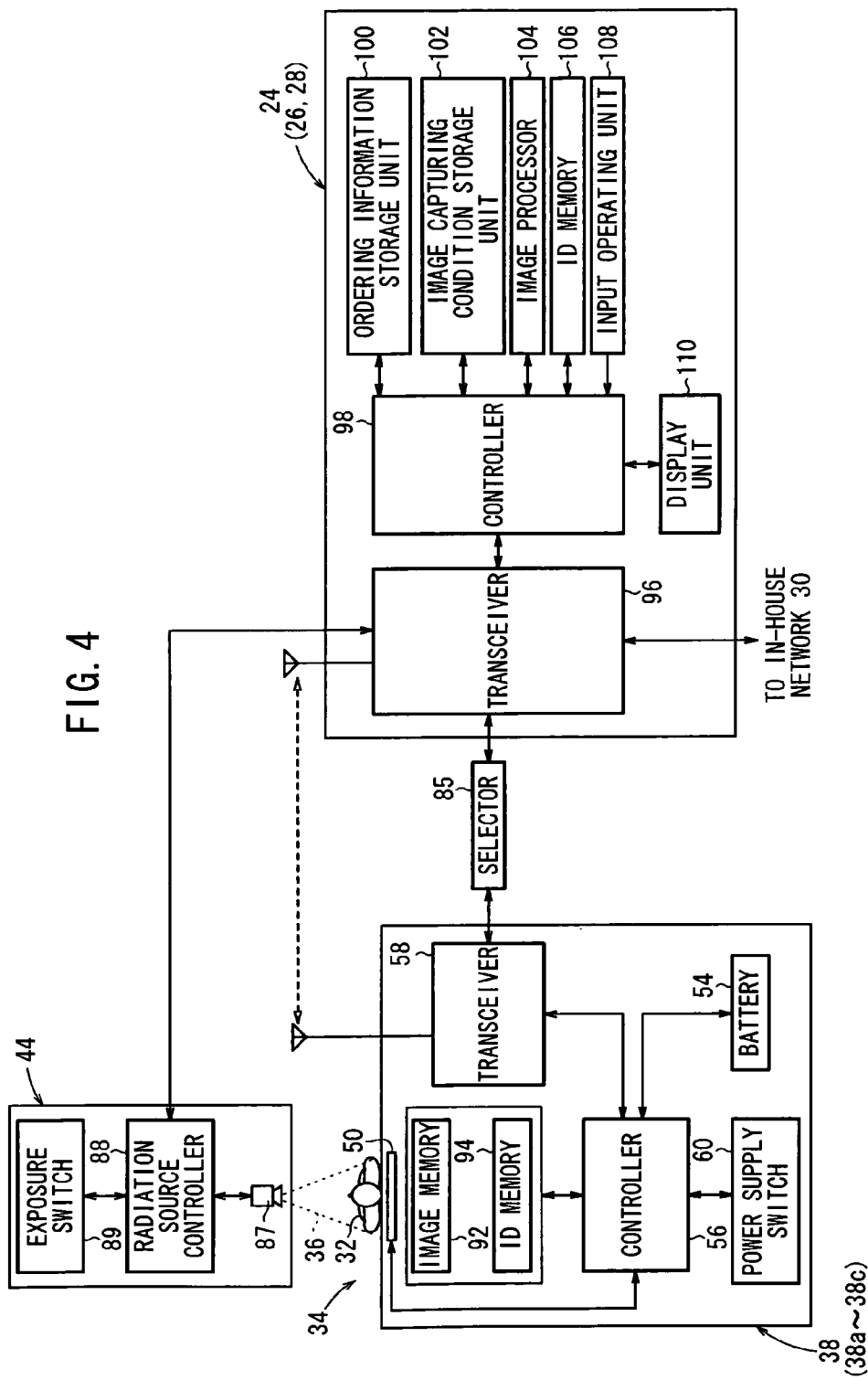
FIG. 4 is a block diagram of a configuration of part of the radiographic image capturing system shown in FIG. 1.

FIG. 4 is a block diagram of the console 24 and the image capturing apparatus 34 which is installed in the image capturing room 18 and which is controlled by the console 24. The consoles 26, 28 and the image capturing rooms 20, 22 are similar in structure to the console 24 and the image capturing room 18, respectively.

The radiation converter 38 of the image capturing apparatus 34 comprises an image memory 92 for storing, as an image signal, a radiographic image from the radiation conversion panel 50, and an ID memory (identification information holding unit) 94 for storing ID information (identification information) for specifying the radiation converter 38.

The console 24 includes a transceiver (second communication unit, wireless transceiver) 96 which sends and receives signals to and from the HIS 12, the RIS 14, the viewer 16, and the consoles 26, 28 via the in-house network 30, and which also sends and receives signals, to and from the image capturing apparatus 34 in the image capturing room 18. The console 24 is controlled by a controller 98.

The controller 98 is connected to an ordering information storage unit (ordering information registration unit) 100, an image capturing condition storage unit (image capturing condition registration unit) 102, an image processor 104, an ID memory (identification information registration unit) 106, an input operating unit (changer) 108, and a display unit (output unit, changer) 110.

Figure 5:
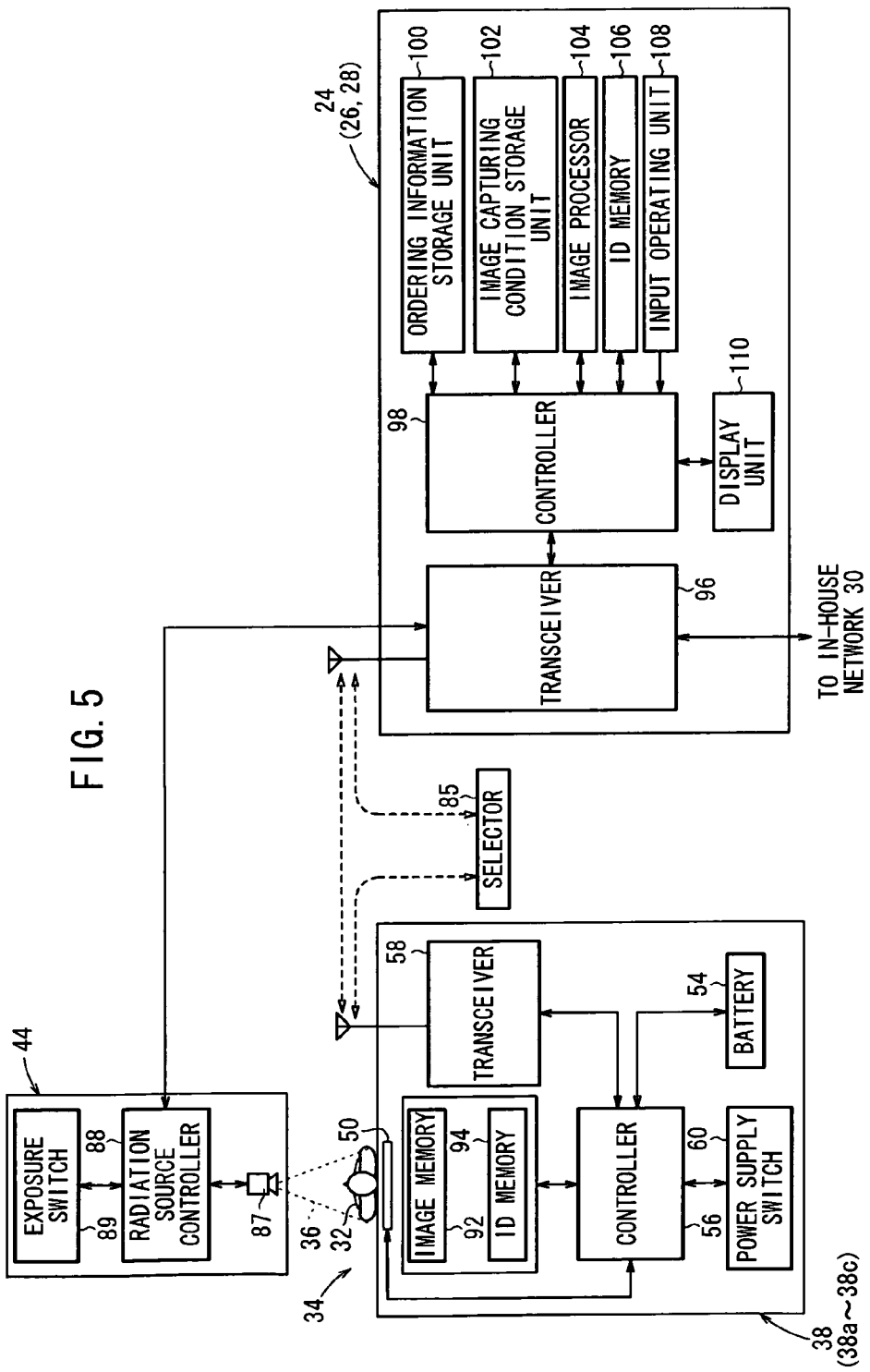
FIG. 5 is a block diagram of a configuration of part of the radiographic image capturing system shown in FIG. 1.

The transceivers 58 of the radiation converters 38 (38a to 38c) and the transceivers 96 of the consoles 24, 26, 28 are connected to a selector (selecting unit) 85. The selector 85 executes a program stored in a memory (not shown) before a radiation source 87 applies radiation 36 to the subject 32 (i.e., before the image-capturing). Thereby, the selector 85 selects one radiation converter and one console that are respectively in the most appropriate communication state in the radiographic image capturing system 10, and associates the selected one radiation converter with the selected one console. Then, the selector 85 sends the association result to the radiation converters 38 and the consoles 24, 26, 28, as an indication signal. In FIG. 4, the selector 85 is connected to the transceivers 58, 96 through wired communication. However, as shown in FIG. 5, the selector 85 may be connected to the transceivers 58, 96 through wireless communication.

Next, the selector 85, a console retrieving unit (selector) 90 included in the radiation converter 38 and having the function of the selector 85, and a radiation converter retrieving unit (selector) 91 included in the console 24, 26, 28 and having the function of the selector 85 will be described below with reference to FIGS. 4 through 12B.

Figure 6A:
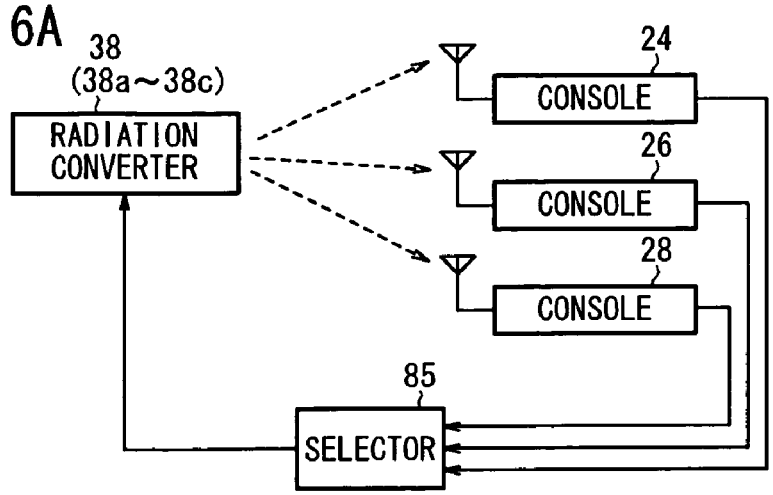
FIG. 6A is an explanatory diagram of selecting one console.

FIGS. 6A through 8B are block diagrams for explaining association processes of the radiation converters with the consoles by the selector 85. FIGS. 6A and 7A show a relationship between one radiation converter 38 (38a to 38c) and three consoles 24, 26, 28. FIGS. 6B and 7B show a relationship between three radiation converters 38a to 38c and one console 24 (26, 28). FIGS. 8A and 8B show a relationship between three radiation converters 38a to 38c and three consoles 24, 26, 28. However, the numbers of the radiation converters and the consoles are not limited to the numbers in FIGS. 6A to 8B.

In FIGS. 6A to 8B, the selector 85 and the radiation converters 38 (38a to 38c) are connected to each other through solid arrows, and the selector 85 and the consoles 24 (26, 28) are also connected to each other through solid arrows. The solid arrows indicate input/output of transmitting/receiving signals between the selector 85 and the radiation converters 38 (38a to 38c) and between the selector 85 and the consoles 24 (26, 28), not indicate wired or wireless communication. Accordingly, in FIGS. 6A to 8B, any of wired communication (FIG. 4) and wireless communication (FIG. 5) is applicable to communication between the selector 85 and the radiation converters 38 (38a to 38c) and between the selector 85 and the consoles 24 (26, 28).

Figure 6B:
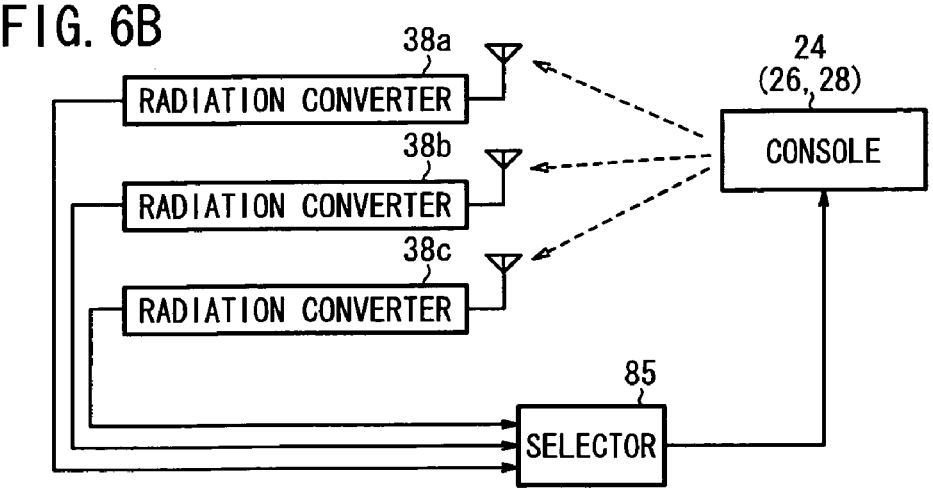
FIG. 6B is an explanatory diagram of selecting one radiation converter.
Figure 7A:
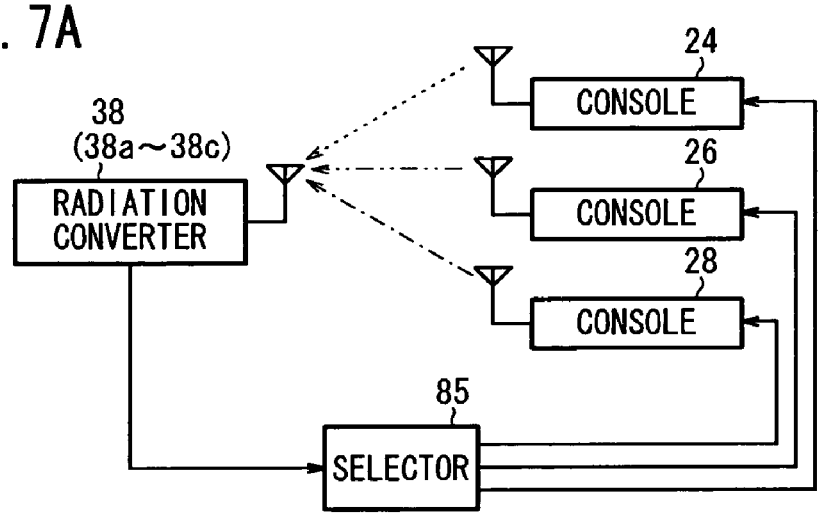
FIG. 7A is an explanatory diagram of selecting one console.
Figure 7B:
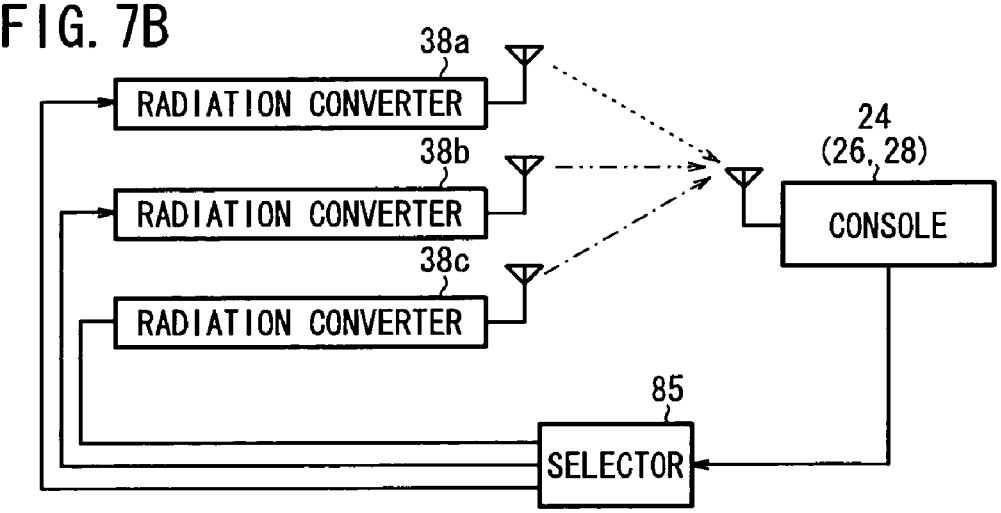
FIG. 7B is an explanatory diagram of selecting one radiation converter.

In FIGS. 6A and 7A, the selector 85 selects one console that is in the most appropriate communication state with one radiation converter 38 from among the consoles 24, 26, 28, and associates the selected console with the radiation converter 38. In FIGS. 6B and 7B, the selector 85 selects one radiation converter that is in the most appropriate communication state with one console 24 (26, 28) from among the radiation converters 38a to 38c, and associates the selected one radiation converter with the console 24 (26, 28). In FIGS. 8A and 8B, the selector 85 selects one radiation converter and one console that are in the most appropriate communication state from among the radiation converters 38a to 38c and the consoles 24, 26, 28, and associates the selected one radiation converter with the selected one console. In FIGS. 8A and 8B, since three radiation converters 38a to 38c and three consoles 24, 26, 28 are provided, there may be up to three combinations of the radiation converters and the consoles.

Detailed explanations will be made below of cases where the selector 85 selects one radiation converter and one console that are respectively in the most appropriate communication state in FIGS. 6A to 8B.

In FIG. 6A, when the selector 85 has a signal detection means (not shown) such as a spectrum analyzer, the selector 85 sends a transmission signal for detection to the transceiver 58 (see FIGS. 4 and 5) of the radiation converter 38 before the image-capturing. The transceiver 58 receives the signal and radiates the signal as radio wave. The transceivers 96 of the consoles 24, 26, 28 receive the radio wave and convert the wave into reception signals. Then, the transceivers 96 send the reception signals to the selector 85.

In this case, the selector 85 selects one console based on at least one of: magnitude of the reception signal levels obtained by the transceivers 96; transmission distance between the transceiver 58 and the transceivers 96 determined from the transmission signal and the reception signals; communication rate (bit rate) between the transceiver 58 and the transceivers 96 determined from the transmission signal and the reception signals; time fluctuation of the reception signal levels; and bit error rate (BER) determined from the transmission signal and the reception signals.

More specifically, if one console is selected based on magnitude of the reception signal levels, the selector 85 selects one console that sends a reception signal having the maximum time-average of the signal levels. In this case, time fluctuation of a reception signal may occur due to radio wave conditions between the transceiver 58 and the transceivers 96. Thus, the selector 85 sends a plurality of transmission signals to the transceiver 58 during a given period of time, and causes the transceiver 58 to perform a plurality of wireless communications with each of the transceivers 96 of the consoles 24, 26, 28. The levels (received electric field intensity) of the reception signals received by each transceiver 96 are measured at a specific frequency, and then the selector 85 selects one console whose time average of the measured field intensity is the largest.

If one console is selected based on transmission distance between the transceiver 58 and the transceivers 96 determined from the transmission signal and the reception signals, the selector 85 selects one console that sends a reception signal representing the shortest transmission distance. In this case, the selector 85 sends, to the transceiver 58, a transmission signal of data having a certain length, and causes the transceiver 58 to perform wireless communication with each of the transceivers 96 of the consoles 24, 26, 28. Then, the selector 85 selects a console that sends a reception signal whose reception completion time (in this case, period of time from the start of transmission of the signal to the transceiver 58 until the completion of reception of the signal by the transceiver 96) is the shortest, as one console that provides the shortest transmission distance. Since the longer transmission distance represents the longer reception completion time, the selector 85 judges the reception signal whose receiving completion time is the shortest, to be the reception signal whose transmission distance is the shortest.

If one console is selected based on bit rate between the transceiver 58 and the transceivers 96, the selector 85 selects one console that sends a reception signal representing the fastest bit rate.

For example, when a radiological technician brings the radiation converter 38 (38a to 38c) to the image capturing room 18 (20, 22), the positional relation between the radiation converter 38 and the consoles 24, 26, 28 changes, thereby changing the communication state between the radiation converter 38 and the consoles 24, 26, 28.

Thus, the selector 85 sends a transmission signal (test data having a certain number of bits) to the transceiver 58 when the technician starts up the radiation converter 38 or at given time points during operation of the radiation converter 38 (i.e., after each radiographic image has been captured, or just before communication is started between the transceivers 58 and 96), and causes the transceiver 58 to perform wireless communication with each of the transceivers 96 of the consoles 24, 26, 28. Then, the selector 85 judges the reception signal that indicates the shortest reception time (transfer time) of the test data, to be the reception signal representing the fastest bit rate, and selects one console that sends the above reception signal.

If one console is selected based on time fluctuation of the reception signal levels, the selector 85 selects one console that sends a reception signal whose time fluctuation of the signal level is the smallest. As in the case where one console is selected based on magnitude of the reception signal level, the selector 85 sends a plurality of transmission signals to the transceiver 58 during a given period of time, and causes the transceiver 58 to perform a plurality of wireless communications with each of the transceivers 96 of the consoles 24, 26, 28. The levels (received electric field intensity) of the reception signals received by each transceiver 96 are measured at a specific frequency, and then the selector 85 selects one console whose time fluctuation of the measured field intensity is the smallest.

If one console is selected based on BER, the selector 85 selects one console that sends a reception signal having the lowest BER. In this case, the selector 85 sends a transmission signal of digital data to the transceiver 58, and causes the transceiver 58 to perform wireless communication with each of the transceivers 96 of the consoles 24, 26, 28. From a reception signal of digital data received by each transceiver 96, the BER in the digital data of the reception signal is calculated with respect to the digital data of the transmission signal, and then the selector 85 selects one console whose BER is the lowest.

When one console has been selected by the above selection process, the selector 85 sends, to the radiation converter 38 (38a to 38c) and the consoles 24, 26, 28, an indication signal indicating that the most appropriate communication state is ensured between one console and one radiation converter 38 (38a to 38c) and that the one console and the one radiation converter 38 (38a to 38c) are associated with each other.

In FIG. 6B, the selector 85 sends a transmission signal to the transceiver 96 of the console 24 (26, 28) before the image-capturing. The transceiver 96 receives the transmission signal and radiates radio wave representing the transmission signal. The transceivers 58 of the radiation converters 38a to 38c receive the radio wave, convert the radio wave into reception signals, and then send the reception signals to the selector 85.

As in the case shown in FIG. 6A, the selector 85 selects one radiation converter based on at least one of: magnitude of the reception signal levels obtained by the transceivers 58; transmission distance between the transceiver 96 and the transceivers 58 determined from the transmission signal and the reception signals; communication rate (bit rate) between the transceiver 96 and the transceivers 58 determined from the transmission signal and the reception signals; time fluctuation of the reception signal levels; and bit error rate (BER) determined from the transmission signal and the reception signals.

More specifically, if one radiation converter is selected based on magnitude of the reception signal levels, the selector 85 selects one radiation converter as follows. That is, the selector 85 sends a plurality of transmission signals to the transceiver 96 during a given period of time, and causes the transceiver 96 to perform a plurality of wireless communications with each of the transceivers 58 of the radiation converters 38a to 38c. The levels (received electric field intensity) of the reception signals received by each transceiver 58 are measured at a specific frequency, and then the selector 85 selects one radiation converter whose time average of the measured field intensity is the largest.

If one radiation converter is selected based on transmission distance between the transceiver 96 and the transceivers 58 determined from the transmission signal and the reception signals, the selector 85 selects one radiation converter as follows. That is, the selector 85 sends, to the transceiver 96, a transmission signal of data having a certain length, and causes the transceiver 96 to perform wireless communication with each of the transceivers 58 of the radiation converters 38a to 38c. Then, the selector 85 selects one radiation converter that sends a reception signal having the shortest reception completion time (in this case, period of time from the start of transmission of the signal to the transceiver 96 until the completion of reception of the signal by the transceiver 58).

If one radiation converter is selected based on communication rate (bit rate) between the transceiver 96 and the transceivers 58 determined from the transmission signal and the reception signals, the selector 85 selects one radiation converter as follows. That is, the selector 85 sends a transmission signal (test data having a certain number of bits) to the transceiver 96, and causes the transceiver 96 to perform wireless communication with each of the transceivers 58 of the radiation converters 38a to 38c. Then, the selector 85 selects one radiation converter that sends a reception signal whose reception time of the test data is the shortest, i.e., a reception signal representing the fastest bit rate.

If one radiation converter is selected based on time fluctuation of the reception signal levels, the selector 85 selects one radiation converter as follows. That is, the selector 85 sends a plurality of transmission signals to the transceiver 96 during a given period of time, and causes the transceiver 96 to perform a plurality of wireless communications with each of the transceivers 58 of the radiation converters 38a to 38c. The signal levels (received electric field intensity) of the reception signals received by each transceiver 58 are measured at a specific frequency, and then the selector 85 selects one radiation converter whose time fluctuation of the measured field intensity is the smallest.

If one radiation converter is selected based on BER, the selector 85 selects one radiation converter as follows. That is, the selector 85 sends a transmission signal of digital data to the transceiver 96, and causes the transceiver 96 to perform wireless communication with each of the transceivers 58 of the radiation converters 38a to 38c. From a reception signal of digital data received by each transceiver 58, a BER in the digital data is calculated, and then the selector 85 selects one radiation converter having the lowest BER.

When one radiation converter has been selected by the above selection process shown in FIG. 6B, the selector 85 sends, to the radiation converters 38a to 38c and the console 24 (26, 28), an indication signal indicating that the most appropriate communication state is ensured between one radiation converter and one console 24 (26, 28) and that the one radiation converter and the one console 24 (26, 28) are associated with each other.

In FIG. 7A, before the image-capturing, the selector 85 performs communication between the console 24 and the radiation converter 38 (38a to 38c), communication between the console 26 and the radiation converter 38 (38a to 38c), and communication between the console 28 and the radiation converter 38 (38a to 38c), at different times. This is because interference of radio waves, reception signals, and the like may occur if the communications are performed at the same time.

In this case, the transceiver 58 of the radiation converter 38 (38a to 38c) functions as a receiver for monitoring the transmission signals. More specifically, the transceiver 58 monitors the transmission signals by converting radio wave from each transceiver 96 into a reception signal. The selector 85 selects one console based on at least one of: magnitude of signal level of (the transmission signal corresponding to) the reception signal from each transceiver 96; transmission distance between the transceivers 96 and the transceiver 58 determined from the transmission signals and the reception signals; communication rate (bit rate) between the transceivers 96 and the transceiver 58 determined from the transmission signals and the reception signals; time fluctuation of signal level of (the transmission signal corresponding to) the reception signal; and BER.

If one console is selected based on magnitude of the signal levels of the transmission signal corresponding to the reception signal, the selector 85 selects one console as follows. That is, the selector 85 sends a plurality of transmission signals to each of the transceivers 96 during a given period of time, and causes each transceiver 96 to perform a plurality of wireless communications with the transceiver 58 at different times. The signal levels (transmitted electric field intensity) of the reception signals received by the transceiver 58 are measured at a specific frequency, and then the selector 85 selects one console that radiates radio wave representing the transmission signal having the largest time average of the measured field intensity.

If one console is selected based on transmission distance between the transceivers 96 and the transceiver 58 determined from the transmission signals and the reception signals, the selector 85 selects one console as follows. That is, the selector 85 sends, to each of the transceivers 96, a transmission signal of data having a certain length, and causes the transceivers 96 of the consoles 24, 26, 28 to perform wireless communications with the transceiver 58 at different times. Then, the selector 85 selects one console that radiates radio wave representing the transmission signal corresponding to the reception signal whose reception completion time is the shortest.

If one console is selected based on communication rate (bit rate) between the transceivers 96 and the transceiver 58, the selector 85 selects one console as follows. That is, the selector 85 sends a transmission signal (test data having a certain number of bits) to each of the transceivers 96, and causes the transceivers 96 to perform wireless communications with the transceiver 58 at different times. Then, the selector 85 selects one console that radiates radio wave representing the transmission signal corresponding to the reception signal having the shortest reception time of the test data.

If one console is selected based on time fluctuation of signal level of the reception signals, the selector 85 selects one console as follows. That is, the selector 85 sends a plurality of transmission signals to each of the transceivers 96 during a given period of time, and causes each of the transceivers 96 to perform a plurality of wireless communications with the transceiver 58 at different times. The signal levels (transmitted electric field intensity) of the reception signals received by the transceiver 58 are measured at a specific frequency, and then the selector 85 selects one console that radiates radio wave representing the transmission signal having the smallest time fluctuation of the measured field intensity.

If one console is selected based on BER, the selector 85 selects one console as follows. That is, the selector 85 sends a transmission signal of digital data to each of the transceivers 96, and causes the transceivers 96 to perform wireless communications with the transceiver 58 at different times. From a reception signal of digital data received by the transceiver 58, the BER in the digital data is calculated, and then the selector 85 selects one console whose BER is the lowest.

When one console has been selected by the selection process shown in FIG. 7A, the selector 85 sends, to the radiation converter 38 (38a to 38c) and the consoles 24, 26, 28, an indication signal indicating that the most appropriate communication state is ensured between one console and one radiation converter 38 (38a to 38c) and that the one console and the one radiation converter 38 (38a to 38c) are associated with each other.

In FIG. 7B, before the image-capturing, the selector 85 performs communication between the radiation converter 38a and the console 24 (26, 28), communication between the radiation converter 38b and the console 24 (26, 28), and communication between the radiation converter 38c and the console 24 (26, 28), at different times.

In this case, the transceiver 96 of the console 24 (26, 28) functions as a receiver for monitoring the transmission signals. The selector 85 selects one radiation converter based on at least one of: magnitude of signal level of (the transmission signal corresponding to) the reception signal obtained by the transceiver 96; transmission distance between the transceivers 58 and the transceiver 96 determined from the transmission signals and the reception signals; communication rate (bit rate) between the transceivers 58 and the transceiver 96 determined from the transmission signals and the reception signals; time fluctuation of signal level of (the transmission signal corresponding to) the reception signal; and BER.

If one radiation converter is selected based on magnitude of the signal levels of the transmission signal corresponding to the reception signal, the selector 85 selects one radiation converter as follows. That is, the selector 85 sends a plurality of transmission signals to each of the transceivers 58 during a given period of time, and causes each transceiver 58 to perform a plurality of wireless communications with the transceiver 96 at different times. The signal levels (transmitted electric field intensity) of the reception signals received by the transceiver 96 are measured at a specific frequency, and then the selector 85 selects one radiation converter that radiates radio wave representing the transmission signal whose time average of the measured field intensity is the largest.

If one radiation converter is selected based on transmission distance between the transceivers 58 and the transceiver 96 determined from the transmission signals and the reception signals, the selector 85 selects one radiation converter as follows. That is, the selector 85 sends, to each of the transceivers 58, a transmission signal of data having a certain length, and causes the transceivers 58 of the radiation converters 38a, 38b, 38c to perform wireless communications with the transceiver 96 at different times. Then, the selector 85 selects one radiation converter that radiates radio wave representing the transmission signal corresponding to the reception signal whose reception completion time is the shortest.

If one radiation converter is selected based on communication rate (bit rate) between the transceivers 58 and the transceiver 96, the selector 85 selects one radiation converter as follows. That is, the selector 85 sends a transmission signal (test data having a certain number of bits) to each of the transceivers 58, and causes the transceivers 58 to perform wireless communications with the transceiver 96 at different times. Then, the selector 85 selects one radiation converter that radiates radio wave representing the transmission signal corresponding to the reception signal having the shortest reception time of the test data.

If one radiation converter is selected based on time fluctuation of signal level of the reception signals, the selector 85 selects one radiation converter as follows. That is, the selector 85 sends a plurality of transmission signals to each of the transceivers 58 during a given period of time, and causes each of the transceivers 58 to perform a plurality of wireless communications with the transceiver 96 at different times. The signal levels (transmitted electric field intensity) of the reception signals received by the transceiver 96 are measured at a specific frequency, and then the selector 85 selects one radiation converter that radiates radio wave representing the transmission signal whose time fluctuation of the measured field intensity is the smallest.

If one radiation converter is selected based on BER, the selector 85 selects one radiation converter as follows. That is, the selector 85 sends a transmission signal of digital data to each of the transceivers 58, and causes the transceivers 58 to perform wireless communications with the transceiver 96 at different times. From a reception signal of digital data obtained by the transceiver 96, the BER in the digital data is calculated, and then the selector 85 selects one radiation converter whose BER is the lowest.

When one radiation converter has been selected by the selection process shown in FIG. 7B, the selector 85 sends, to the radiation converters 38a to 38c and the console 24 (26, 28), an indication signal indicating that the most appropriate communication state is ensured between one radiation converter and one console 24 (26, 28) and that the one radiation converter and the one console 24 (26, 28) are associated with each other.

FIG. 8A shows a selection process in a case where three radiation converters 38a to 38c and three consoles 24, 26, 28 are provided, which is a simply-extended process of the selection process in the case where one radiation converter 38 (38a to 38c) and three consoles 24, 26, 28 are provided (see FIG. 6A) or the selection process in the case where three radiation converters 38a to 38c and one console 24 (26, 28) are provided (see FIG. 7B). When the selection process shown in FIG. 6A is extended to the selection process shown in FIG. 8A, the process shown in FIG. 6A may be applied to each of the radiation converters 38a to 38c in FIG. 8A. When the selection process shown in FIG. 7B is extended to the selection process shown in FIG. 8A, the process shown in FIG. 7B may be applied to each of the consoles 24, 26, 28 in FIG. 8A.

FIG. 8B shows a selection process in the case where three radiation converters 38a to 38c and three consoles 24, 26, 28 are provided, which is a simply-extended process of the selection process in the case where three radiation converters 38a to 38c and one console 24 (26, 28) are provided (see FIG. 6B) or the selection process in the case where one radiation converter 38 and three consoles 24, 26, 28 are provided (see FIG. 7A) is simply applied. When the selection process shown in FIG. 6B is extended to the selection process shown in FIG.

8B, the process shown in FIG. 6B may be applied to each of the consoles 24, 26, 28 in FIG. 8B. When the selection process shown in FIG. 7A is extended to the selection process shown in FIG. 8B, the process shown in FIG. 7A may be applied to each of the radiation converters 38a to 38c in FIG. 8B.

In FIGS. 6A through 8B, the explanations have been made in the cases where the selector 85 sends a transmission signal to the radiation converter 38 (38a to 38c) or to the console 24 (26, 28). However, the present invention is not limited in this respect. For example, the controller 56 of the radiation converter 38 (38a to 38c) or the controller 98 of the console 24 (26, 28) may generate a transmission signal. In this case, when the selector 85 sends a control signal for instructing the controller 56, 98 to generate the transmission signal, to the radiation converter 38 (38a to 38c) or to the console 24 (26, 28), the controller 56 or 98 can generate and output the transmission signal to the transceiver 58 or 96.

Figure 10A:
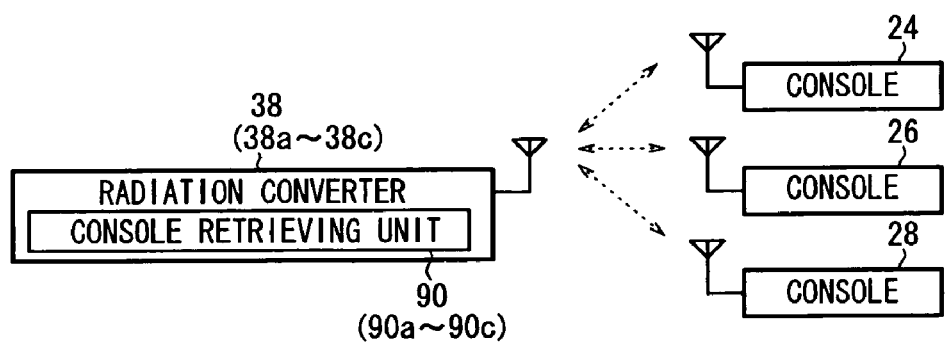
FIG. 10A is an explanatory diagram of selecting one console.
Figure 10B:
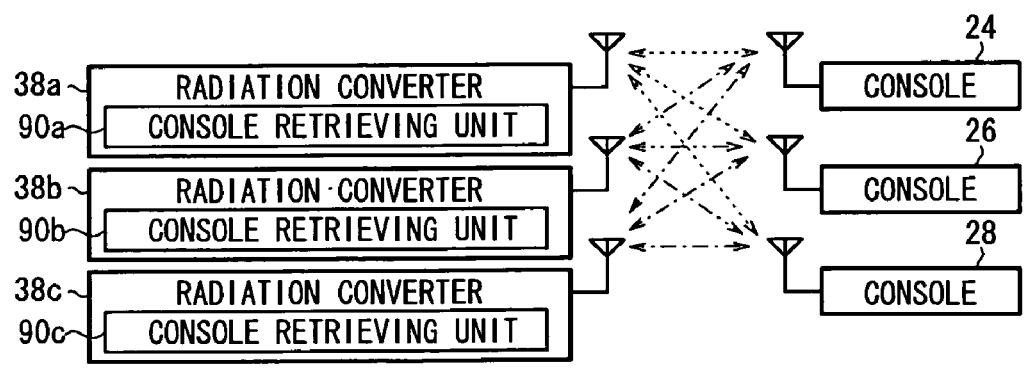
FIG. 10B is an explanatory diagram of selecting one radiation converter and one console.
Figure 11:
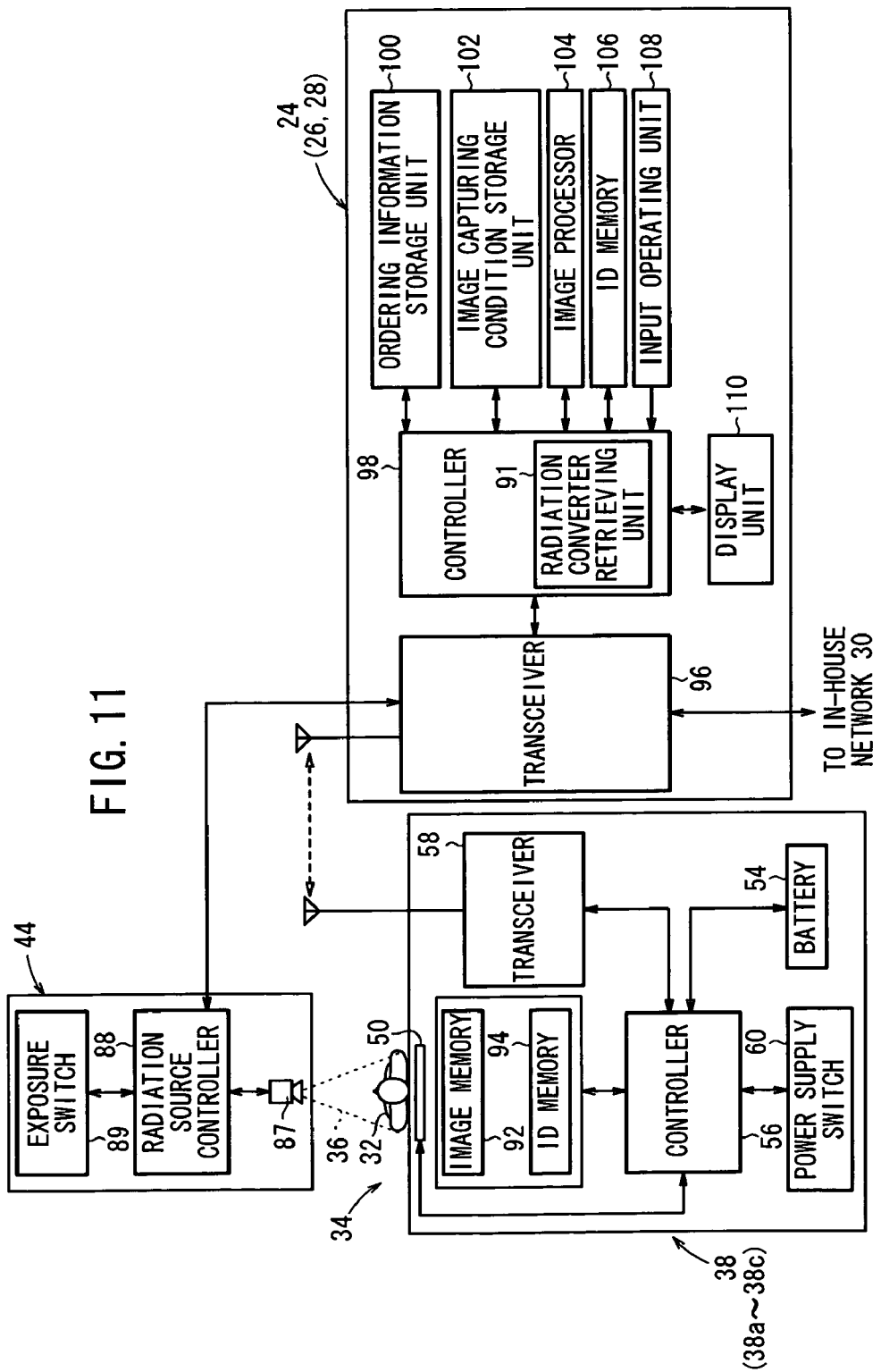
FIG. 11 is a block diagram of another configuration of part of the radiographic image capturing system shown in FIG. 1.

Also, as shown in FIGS. 9 to 10B, the console retrieving unit 90 (90a to 90c) having the function of the selector 85 may be incorporated in the radiation converter 38 (38a to 38c). Alternatively, as shown in FIGS. 11 to 12B, the radiation converter retrieving unit 91 having the function of the selector 85 may be incorporated in the console 24 (26, 28).

If the radiation converter 38 (38a to 38c) includes the console retrieving unit 90 (90a to 90c), the selection processes in FIGS. 6A and 7A can be applied.

When the selection process in FIG. 6A is applied, the console retrieving unit 90 (90a to 90c) outputs a transmission signal to the transceiver 58, and the transceiver 58 radiates radio wave representing the transmission signal. The transceivers 96 of the consoles 24 (26, 28) receive the radio wave, and convert the radio wave into reception signals. The controllers 98 of the consoles 24 (26, 28) control the transceivers 96 to send data indicating the signal levels of the reception signals to the transceiver 58. The console retrieving unit 90 (90a to 90c) can recognize the signal levels of the reception signals based on the data received through the transceiver 58. Thus, the selection process in FIG. 6A can be performed.

When the selection process in FIG. 7A is applied, the console retrieving unit 90 (90a to 90c) outputs a control signal to the transceiver 58, and the transceiver 58 sends the control signal to the controllers 98 of the consoles 24 (26, 28) through the transceivers 96. The controllers 98 receive the control signal, and generate transmission signals based on the received control signal. Then the controllers 98 control the transceivers 96 to radiate radio wave representing the generated transmission signals. Also, in this case, the console retrieving unit 90 (90a to 90c) can perform the selection process in FIG. 7A based on the reception signals received via the transceiver 58.

The transceiver 58 is capable of sending/receiving signals to and from the consoles 24, 26, 28 by UWB or wireless LAN. Thus, if the transceiver 58 is a wireless transceiver for sending/receiving signals by UWB, the console retrieving unit 90 (90a to 90c) can use the transceiver 58 as a short-range radar for searching for the console 24, 26, 28 by UWB. Alternatively, if the transceiver 58 is a wireless transceiver for sending/receiving signals by wireless LAN, the console retrieving unit 90 (90a to 90c) can use the transceiver 58 as a position detecting mechanism for detecting the position of the consoles 24, 26, 28. In this case, the console retrieving unit 90 (90a to 90c) determines the transmission distance based on the distance obtained by the short-range radar or based on the position obtained by the position detecting mechanism, and then selects one console having the shortest determined transmission distance.

As described above, when the console retrieving unit 90 (90a to 90c) associates one radiation converter with one console, an indication signal indicating the association result is sent to the other radiation converters and the consoles 24, 26, 28 via the transceiver 58.

On the other hand, when the console 24 (26, 28) includes the radiation converter retrieving unit 91, the selection processes in FIGS. 6B and 7B can be applied.

When the process in FIG. 6B is applied, the radiation converter retrieving unit 91 outputs a transmission signal to the transceiver 96. The transceiver 96 receives the transmission signal and radiates radio wave representing the received transmission signal. The transceiver 58 of each radiation converter 38 (38a to 38c) receives the radio wave, and converts the radio wave into a reception signal. The controller 56 of each radiation converter 38 (38a to 38c) controls the transceiver 58 to send data indicating the signal level of the reception signal to the transceiver 96. The radiation converter retrieving unit 91 can recognize the signal level of each reception signal based on each data received via the transceiver 96. Thus, the selection process in FIG. 6B can be performed.

When the selection process in FIG. 7B is applied, the radiation converter retrieving unit 91 outputs a control signal to the transceiver 96, and the transceiver 96 sends the control signal to the controller 56 of each radiation converter 38 (38a to 38c) through the transceiver 58. Each controller 56 receives the control signal, and generates a transmission signal based on the received control signal. Then the controller 56 controls the transceiver 58 to radiate radio wave representing the generated transmission signal. Also, in this case, the radiation converter retrieving unit 91 can perform the selection process in FIG. 7B based on each reception signal received via the transceiver 96.

The transceiver 96 may be used as a short-range radar for searching for the radiation converter 38 (38a to 38c) by UWB. Alternatively, if the transceiver 96 is a wireless transceiver for sending/receiving signals by wireless LAN, the transceiver 96 may be used as a position detecting mechanism for detecting the position of the radiation converter 38 (38a to 38c). In this case, the radiation converter retrieving unit 91 determines the transmission distance based on the distance obtained by the short-range radar or based on the position obtained by the position detecting mechanism, and then selects one radiation converter having the shortest determined transmission distance.

As described above, when the radiation converter retrieving unit 91 associates one radiation converter with one console, an indication signal indicating the association result is sent to the radiation converters 38a to 38c and the other consoles via the transceiver 96.

As described above, the association process of one console and one radiation converter is described with reference to FIGS. 4 to 12B. After the association process has ensured a communication state between one console and one radiation converter, an image of the subject 32 is captured. In this case, when the radiation source 87 applies radiation 36 to the subject 32 and an image of the subject 32 is captured, the transceiver 58 associates the radiographic image stored in the image memory 92 with the ID information, and sends the associated radiographic image to the console 24 by wireless communication.

The radiation generator 44 of the image capturing apparatus 34 includes the radiation source 87 for emitting radiation 36, a radiation source controller 88 for controlling the radiation source 87, and an exposure switch 89.

In the console 24, the ordering information storage unit 100 stores (registers) the image-capturing ordering information obtained from the RIS 14. The ordering information is generated by the doctor using the RIS 14. The ordering information includes patient information including the name, age, gender, etc. about the patient, i.e., the subject 32, and an image capturing apparatus 34 to be used for capturing a radiographic image of the subject 32, a body region of the subject 32 which is to be imaged, an image capturing method, and image capturing conditions. The image capturing conditions are conditions for determining a dose of radiation to be applied to the subject 32, e.g., a tube voltage and a tube current of the radiation source 87, an irradiation time, etc.

The image capturing condition storage unit 102 stores (registers) image capturing conditions for the image capturing apparatus 34 which have been obtained from the RIS 14 or set by the radiological technician through the console 24. The image processor 104 performs image processing on the radiographic image obtained from the image capturing apparatus 34.

In the ID memory 106, the ID information for the radiation converters 38 is stored beforehand. The input operating unit 108 is an input means such as a keyboard or a mouse. The technician operates the input operating unit 108 to input certain information. The display unit 110 displays radiographic image processed by the image processor 104.

When the transceiver 96 receives the indication signal from the selector 85 or from the console retrieving unit 90 (90a to 90c) or when the radiation converter retrieving unit 91 generates the indication signal, the controller 98 displays information representing the association of one console with one radiation converter on the display unit 110, based on the indication signal, while changes the ordering information stored in the ordering information storage unit 100 and the image capturing conditions stored in the image capturing condition storage unit 102 depending on the association.

In this case, for example, if the radiation converter 38 in the image-capturing room 18 is associated with the console 26 connected to the image-capturing room 20 or with the console 28 connected to the image-capturing room 22 by the selector 85, the console retrieving unit 90 (90a to 90c) or the radiation converter retrieving unit 91, the radiological technician operates the input operating unit 108 in order to change the above association into the new association of the radiation converter 38 with the console 24 connected to the image-capturing room 18 where the radiation converter 38 is present. Based on the input operation, the controller 98 changes the association such that the radiation converter 38 is newly associated with the console 24. Further, the controller 98 displays the changed association on the display unit 110, while changes the ordering information stored in the ordering information storage unit 100 and the image capturing conditions stored in the image capturing condition storage unit 102 depending on the changed association.

When the technician brings the radiation converter 38 into the image-capturing room 18 and captures an image of the subject 32 using the radiation converter 38 in the image-capturing room 18, if the radiation converter 38 in the image-capturing room 18 is associated with the console 26 connected to the image-capturing room 20 or with the console 28 connected to the image-capturing room 22, eventually the subject 32 and the radiation converter 38 need to be moved from the image-capturing room 18 to the image-capturing room 20 or 22. This imposes burden on the subject 32. Also, it is time-consuming to change the image-capturing in the image-capturing room 18 into the image-capturing in the image-capturing room 20 or 22, resulting in a longer working time of the technician for preparing the image-capturing (reduction in working efficiency). Thus, burden on the technician also increases and efficiency of image-capturing decreases accordingly.

According to the present invention, the technician can operate the input operating unit 108 to change the association by the selector 85, the console retrieving unit 90 (90a to 90c) or the radiation converter retrieving unit 91 into an association desired by the technician. Thus, the above-mentioned problems are prevented, and burdens on the subject 32 as well as the technician are reduced. Further, reduction in the image-capturing preparation time and improvement in the efficiency of image-capturing can be achieved.

The radiographic image capturing system 10 according to the present invention is basically constructed as above. Next, operation of mainly the console 24 and the image-capturing room 18 will be described below with reference to a flowchart shown in FIG. 13.

Figure 13:
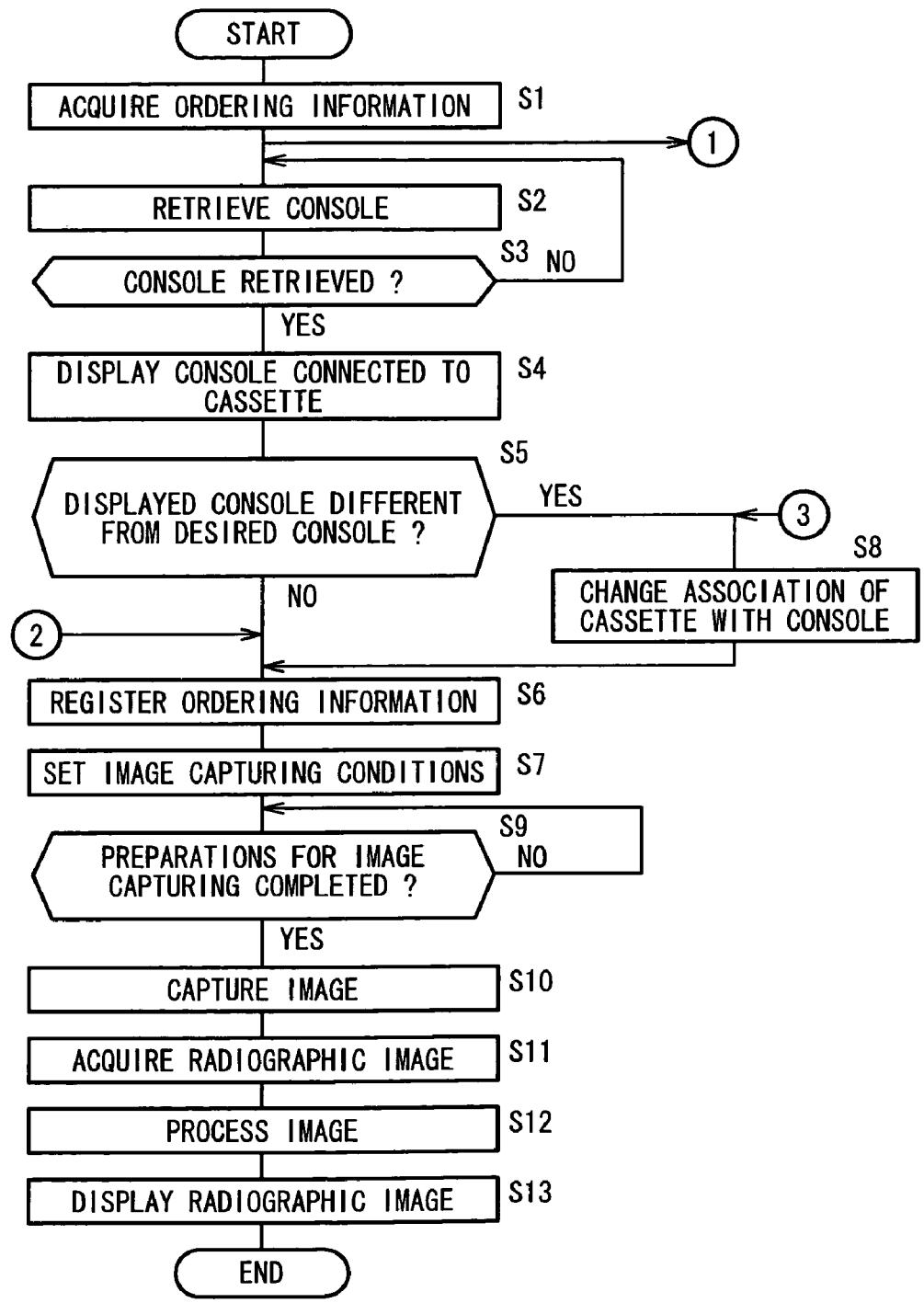
FIG. 13 is a flowchart of an operation sequence of the radiographic image capturing system according to the embodiment of the present invention.

The flowchart in FIG. 13 shows a case where an image of the subject 32 is captured using the radiation converter 38 in the image-capturing room 18. In this case, if the radiation converter 38 in the image-capturing room 18 is associated with the console 24 connected to the image-capturing room 18, burdens on the subject 32 and the technician can be reduced while reduction in the image-capturing preparation time and improvement in the efficiency of image-capturing can be achieved.

Any of the processes in FIGS. 6A, 7A and 10A may be applied to the flowchart in FIG. 13. In the below explanations, the process in FIG. 6A is applied.

The transceiver 96 of the console 24 acquires image-capturing ordering information from the RIS 14 through the in-house network 30 (step S1).

When the controller 98 receives the ordering information, the ordering information storage unit 100 stores therein the ordering information while the image capturing condition storage unit 102 stores therein image capturing conditions included in the ordering information.

Meanwhile, the radiological technician brings the radiation converter 38 into the image-capturing room 18. When the technician turns on the power supply switch 60 of the radiation converter 38, the selector 85 executes the program stored in the memory (not shown) to send a transmission signal to the transceiver 58 of the radiation converter 38, in step S2. The transceiver 58 receives the transmission signal, and radiates radio wave representing the received transmission signal. The transceivers 96 of the consoles 24, 26, 28 receive the radio wave, convert the received radio wave into reception signals, and send the reception signals to the selector 85. The selector 85 receives the receptions signals and compares the received reception signals from the consoles 24, 26, 28, based on at least one of: magnitude of the signal level of the reception signal from each transceiver 96; transmission distance between the transceivers 58 and 96 determined from the transmission and reception signals; communication rate between the transceivers 58 and 96 determined from the transmission and reception signals; time fluctuation of the signal level of each reception signal; and BER determined from the transmission and reception signals, and then the selector 85 retrieves (selects) one console that has the most appropriate communication state with the radiation converter 38.

When the one console has been retrieved (step S3: YES), the selector 85 sends an indication signal indicating that the most appropriate wireless communication can be established between the one console and the radiation converter 38 and that the one console has been associated with the radiation converter 38, to the radiation converter 38 and the consoles 24, 26, 28. When the radiation converter 38 and the consoles 24, 26, 28 receive the indication signal, the radiation converter 38 and the consoles 24, 26, 28 recognize the one console and the radiation converter 38 that have been associated with each other by the selector 85.

Based on the received indication signal, the controller 98 of each console 24, 26, 28 displays information representing the association of the one console with the radiation converter 38 on the display unit 110 (step S4), and changes the ordering information stored in the ordering information storage unit 100 and the image capturing conditions stored in the image capturing condition storage unit 102 depending on the association.

In step S3, when the selector 85 can not retrieve the one console (step S3: NO), the process in step S2 is performed again. Incidentally, the radiation converter 38 brought into the image-capturing room 18 may be loaded into the cradle 40 for charging the battery 54 of the radiation converter 38.

In step S5, the technician visually recognizes the information displayed on the display unit 110, and confirms whether or not the one console associated with the radiation converter 38 is different from the console 24 connected to the image-capturing room 18 having the radiation converter 38. That is, since the radiation converter 38 is in the image-capturing room 18, if the radiation converter 38 is associated with the console 24 connected to the image-capturing room 18, the image-capturing in the image-capturing room 18 reduces burdens on the subject 32 and the technician, and then working efficiency in the image-capturing preparation and the image-capturing are improved. Stated otherwise, if the image capturing process is performed in the association of the console 24 with the radiation converter 38, the technician performs the image-capturing process smoothly.

In step S5, if the information displayed on the display unit 110 indicates the desired association of the one console 24 with the radiation converter 38 (step S5: NO), the technician operates the input operating unit 108 to input information to accept the image-capturing process using the associated console 24 and radiation converter 38. Thereby, the ordering information stored in the ordering information storage unit 100 is fixed as ordering information in the accepted image capturing process (step S6), while the image capturing conditions stored in the image capturing condition storage unit 102 are fixed as image capturing conditions in the accepted image capturing process (step S7).

On the other hand, in step S5, the information displayed on the display unit 110 indicates the undesired association of the console 26 or 28 with the radiation converter 38, i.e., the displayed association is different from the desired association of the console 24 with the radiation converter 38, (step S5: YES), the technician operates the input operating unit 108 to input information to change the undesired association of the console 26 or 28 with the radiation converter 38 into the desired association of the console 24 with the radiation converter 38.

Based on the input information, the controller 98 changes the association of the console 26 or 28 with the radiation converter 38 into the association of the console 24 with the radiation converter 38. Then, the controller 98 displays information indicating the changed association of the console 24 with the radiation converter 38 on the display unit 110, and changes the ordering information stored in the ordering information storage unit 100 and the image capturing conditions stored in the image capturing condition storage unit 102 depending on the changed association (step S8).

As a result, in the ordering information storage unit 100, the ordering information corresponding to the changed association is registered as the ordering information in the image capturing process (step S6), while in the image capturing condition storage unit 102, the image capturing conditions corresponding to the changed association are registered as the image capturing conditions in the image capturing process (step S7).

As described above, the necessary ordering information and image capturing conditions are registered. Thereafter, the console 24 sends and sets the image capturing conditions with respect to the radiation generator 44 of the image capturing apparatus 34 according to the ordering information. After the image capturing conditions is set in the radiation generator 44, and preparations for the image capturing process are finished (step S9: YES), the image capturing process is started (step S10).

In this case, the radiation converter 38 having the battery 54 that has been charged by the cradle 40 is placed on the image capturing base 42, and the subject 32 is positioned on the radiation converter 38. Then, the technician operates the exposure switch 89 to cause the radiation source 87 to apply radiation 36 to the subject 32. The radiation 36 passes through the subject 32, and is irradiated to the radiation conversion panel 50 of the radiation converter 38. Thus, a radiographic image of the subject 32 is captured.

The radiation 36 is converted into electric signals by the photoelectric conversion layer 62 of the pixels 68 of the radiation conversion panel 50. The electric signals are stored as electric charges in the storage capacitors 66. The stored electric charges, which represent radiographic image of the subject 32, are read from the storage capacitors 66 according to address signals, which are supplied from the controller 56 to the line scanning driver 74 and the multiplexer 76.

More specifically, in response to the address signal supplied from the controller 56, the address decoder 78 of the line scanning driver 74 outputs a selection signal to select one of the switches SW1, which supplies the control signal Von to the gates of the TFTs 64 connected to the gate line 70 corresponding to the selected switch SW1. In response to the address signal supplied from the controller 56, the address decoder 84 of the multiplexer 76 outputs a selection signal to successively turn on the switches SW2 to switch between the signal lines 72, for thereby reading through the signal lines 72 the electric charges stored in the storage capacitors 66 of the pixels 68 connected to the selected gate line 70.

The electric charges read from the storage capacitors 66 of the pixels 68 connected to the selected gate line 70 are amplified by the respective amplifiers 80, sampled by the sample and hold circuits 82, and supplied to the multiplexer 76. Based on the supplied electric charges, the multiplexer 76 generates and supplies a radiographic image signal to the A/D converter 86, which converts the radiographic image signal into digital signals. The controller 56 controls the transceiver 58 to send the converted digital signals to the console 24 by wireless communication.

Similarly, the address decoder 78 of the line scanning driver 74 successively turns on the switches SW1 to switch between the gate lines 70 according to the address signal supplied from the controller 56. The electric charges stored in the storage capacitors 66 of the pixels 68 connected to the successively selected gate lines 70 are read through the signal lines 72, and processed by the multiplexer 76 and the A/D converter 86 into digital signals. The controller 56 controls the transceiver 58 to send the digital signals to the console 24 by wireless communication.

In this case, the controller 56 sends the ID information and the radiographic image from the transceiver 58 to the console 24 by wireless communication.

If the received ID information is stored in the ID memory 106 and coincides with the ID information of the associated radiation converter 38 indicated by the indication signal, the controller 98 of the console 24 outputs the radiographic image that has been received together with the received ID information, to the image processor 104 (step S11). The image processor 104 processes the input radiographic image (step S12). The controller 98 displays the processed radiographic image on the display unit 110 (step S13). Further, the processed radiographic image is sent to the viewer 16 via the in-house network 30 for a doctor to interpret the radiographic image for diagnosis.

The flowchart in FIG. 13 shows the case where a plurality of consoles 24, 26, 28 and one radiation converter 38 are provided. That is, one console is selected from among the consoles 24, 26, 28, and the selected one console is associated with the radiation converter 38. Then, the associated console and radiation converter 38 are used for the image capturing process.

Figure 14:
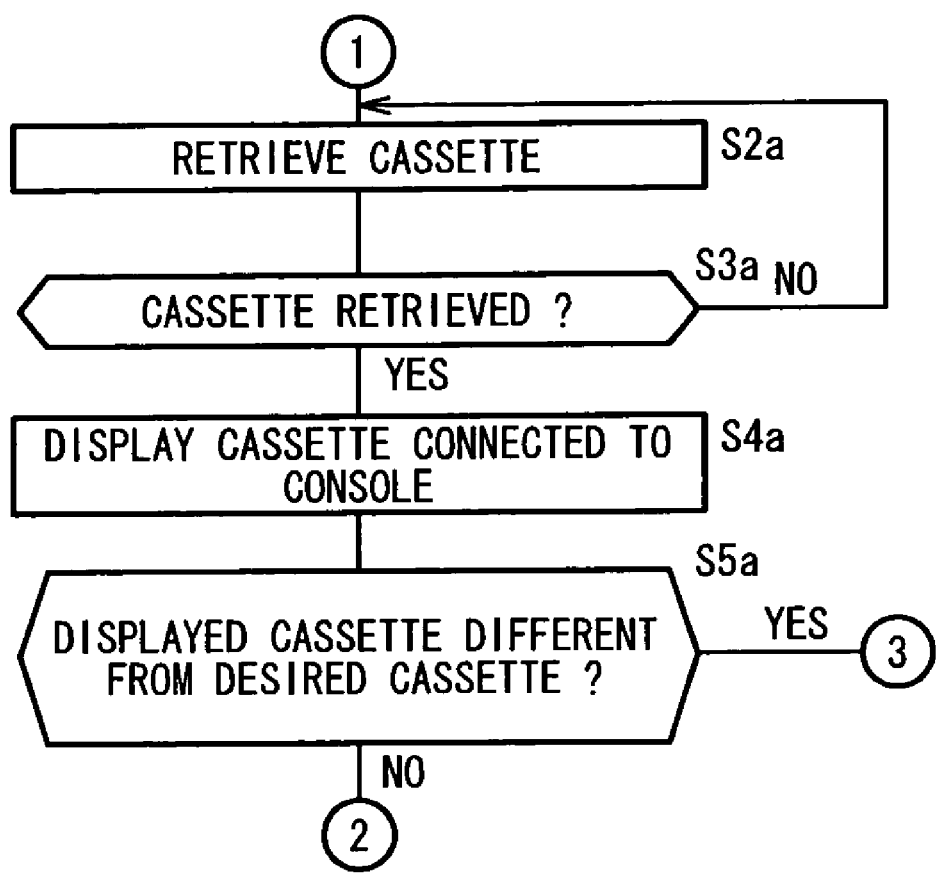
FIG. 14 is a flowchart into which the flowchart shown in FIG. 13 is partly modified.

However, the radiographic image capturing system 10 according to the present embodiment is not limited to the case of the flowchart in FIG. 13, and may be applied to a flowchart shown in FIG. 14. The flowchart in FIG. 14 shows a case where a plurality of radiation converters 38a to 38c and one console 24 (26, 28) are provided. In this case, one radiation converter is selected from among the radiation converters 38a to 38c, and the selected one radiation converter is associated with the console 24 (26, 28). Then, the associated radiation converter and console 24 (26, 28) are used to capture a radiographic image.

The processes in FIGS. 6B, 7B and 12A may be applied in order to execute the flowchart in FIG. 14. In the below explanation, the process in FIG. 6B is applied as an example. Also, the flowchart in FIG. 14 will be described below in the case where the console 24 connected to the image-capturing room 18 is associated with one of the radiation converters 38a to 38c.

In step S2a, the selector 85 sends a transmission signal to the transceiver 96 of the console 24. The transceiver 96 receives the transmission signal, and radiates radio wave representing the received transmission signal. The transceivers 58 of the radiation converters 38a to 38c receive the radio wave, and convert the received radio wave into reception signals, which are sent to the selector 85. The selector 85 receives the reception signals and compares the received reception signals from the radiation converters 38a to 38c, based on at least one of: magnitude of the signal level of the reception signal from each transceiver 58; transmission distance between the transceivers 96 and 58 determined from the transmission and reception signals; communication rate between the transceivers 96 and 58 determined from the transmission and reception signals; time fluctuation of the signal level of each reception signal; and BER determined from the transmission and reception signals, and then the selector 85 retrieves (selects) one radiation converter that has the most appropriate communication state with the console 24.

When the one radiation converter has been retrieved (step S3a: YES), the selector 85 sends an indication signal indicating that the most appropriate wireless communication can be established between the one radiation converter and the console 24 and that the one radiation converter has been associated with the console 24, to the radiation converters 38a to 38c and the console 24. When the radiation converters 38a to 38c and the console 24 receive the indication signal, the radiation converters 38a to 38c and the console 24 recognize the one radiation converter and the console 24 that have been associated with each other by the selector 85.

Based on the received indication signal, the controller 98 of the console 24 displays information representing the association of the one radiation converter with the console 24 on the display unit 110 (step S4a), and change the ordering information stored in the ordering information storage unit 100 and the image capturing conditions stored in the image capturing condition storage unit 102 depending on the association.

In step S3a, when the selector 85 can not retrieve the one radiation converter (step S3a: NO), the process in step S2a is performed again.

In step S5a, the technician visually recognizes the information displayed on the display unit 110, and confirms whether the one radiation converter associated with the console 24 is present in the image-capturing room 18 or not. If the information indicates the association of the radiation converter in the image-capturing room 18 with the console 24, i.e., if the information indicates the desired radiation converter (step S5a: NO), the process of step S6 and the subsequent processes in FIG. 13 are performed.

Conversely, in step S5a, the information on the display unit 110 indicates the association of the radiation converter out of the image-capturing room 18 with the console 24, i.e., if the information indicates a radiation converter different from the desired radiation converter (step S5a: YES), the process moves to step S8. In this case, the technician operates the input operating unit 108 to input information to change the current association into the new association of the radiation converter in the image-capturing room 18 with the console 24.

The radiographic image capturing system 10 according to the present embodiment may be applied to a case of a flowchart shown in FIG. 15, instead of the flowcharts in FIGS. 13 and 14. The flowchart in FIG. 15 shows the case where a plurality of the radiation converters 38a to 38c and a plurality of the consoles 24, 26, 28 are provided. In this case, one radiation converter is selected from among the radiation converters 38a to 38c, while one console is selected from among the consoles 24, 26, 28, and the selected radiation converter is associated with the selected console. Then, the associated radiation converter and console are used to capture a radiographic image.

The processes in FIGS. 8A, 8B, 10B and 12B may be applied in order to execute the flowchart in FIG. 15. In the below explanation, the process in FIG. 8A is applied as an example.

In step S2b, the selector 85 sends transmission signals to the radiation converters 38a to 38c at different times, and receives reception signals depending on the transmission signals, from the consoles 24, 26, 28. The selector 85 receives the reception signals and compares the received reception signals from the consoles 24, 26, 28, based on at least one of: magnitude of the signal level of the reception signal from each transceiver 96; magnitude of the signal level of the transmission signal corresponding to the reception signal; transmission distance between the transceivers 58 and 96 determined from the transmission and reception signals; communication rate between the transceivers 58 and 96 determined from the transmission and reception signals; time fluctuation of the signal level of each reception signal; time fluctuation of the signal level of each transmission signal; and BER determined from the transmission and reception signals, and then the selector 85 retrieves (selects) one radiation converter and one console that have the most appropriate communication state therebetween.

When the one radiation converter and the one console have been retrieved (step S3b: YES), the selector 85 sends an indication signal indicating that the most appropriate wireless communication can be established between the one radiation converter and the one console and that the one console has been associated with the one radiation converter, to the radiation converters 38a to 38c and the consoles 24, 26, 28. When the radiation converters 38a to 38c and the consoles 24, 26, 28 receive the indication signal, the radiation converters 38a to 38c and the consoles 24, 26, 28 recognize the one radiation converter and the one console that have been associated with each other by the selector 85.

Based on the received indication signal, the controllers 98 of the consoles 24, 26, 28 display information representing the association of the one console with the one radiation converter on the display units 110 (step S4b), and change the ordering information stored in the ordering information storage unit 100 and the image capturing conditions stored in the image capturing condition storage unit 102 depending on the association.

In step S3b, when the selector 85 can not retrieve the one radiation converter and/or the one console (step S3b: NO), the process in step S2b is performed again.

In step S5b, the technician visually recognizes the information displayed on any one of the display units 110. If the information indicates the association of the desired radiation converter with the desired console (step S5b: NO), the process of step S6 and the subsequent processes in FIG. 13 are performed.

Conversely, in step S5b, if the information on the display unit 110 indicates the association of the undesired radiation converter with the undesired console, i.e., if the displayed radiation converter and console are not the desired ones (step S5b: YES), the process moves to step S8. In this case, the technician operates the input operating unit 108 to input information to change the current association into the desired association.

As described above, according to the present embodiment, the selector 85, the console retrieving unit 90 (90a to 90c) or the radiation converter retrieving unit 91 automatically selects one radiation converter and one console (processor) that have the most appropriate communication state, and also automatically associates the selected radiation converter with the selected console. Thus, the technician oneself does not need to perform the association process, and the association process can be performed efficiently.

Since one radiation converter and one console that are placed in the most appropriate communication state are selected, the communication state between the one radiation converter and the one console is ensured thereby to send/receive a radiographic image stably.

Also, the radiation converters 38 (38a to 38c) each include the transceiver 58 for communicating with external devices. The consoles 24, 26, 28 each include the transceiver 96 for communicating with external devices. The console retrieving unit 90 (90a to 90c) or the radiation converter retrieving unit 91 selects one radiation converter and one console that have the most appropriate communication state between the transceivers 58 and 96, associates the selected radiation converter with the selected console, and sends (outputs) an indication signal indicating the association result.

Owing to this, the radiation converters 38 (38a to 38c) and the consoles 24, 26, 28 can recognize which radiation converter is associated with which console.

In this case, since the selector 85 is provided separately from the radiation converters 38 (38a to 38c) and the consoles 24, 26, 28, the selector 85 functions as an access point for distributing communications when the association process is performed. As a result, wireless communication can be performed efficiently between the radiation converters 38 (38a to 38c) and the consoles 24, 26, 28 when the association process is performed. Also, since the selector 85 is provided separately from the radiation converters 38 (38a to 38c), a reduced size and low price can be achieved in the radiation converter 38 (38a to 38c).

In all cases: where a plurality of the radiation converters 38a to 38c and a plurality of the consoles 24, 26, 28 are provided; where one radiation converter 38 (38a to 38c) and a plurality of the consoles 24, 26, 28 are provided; and where a plurality of the radiation converters 38a to 38c and one console 24, 26, 28 are provided, the selector 85 can associate one radiation converter with one console efficiently.

The console retrieving unit 90 (90a to 90c) is suitable for the association process in the case where one radiation converter 38 (38a to 38c) and a plurality of the consoles 24, 26, 28 are provided. The radiation converter retrieving unit 91 is suitable for the association process in the case where a plurality of the radiation converters 38 (38a to 38c) and one console 24 (26, 28) are provided.

The selector 85, the console retrieving unit 90 (90a to 90c), or the radiation converter retrieving unit 91 selects one radiation converter and one console based on at least one of: signal level of the transmission signal; signal level of the reception signal; transmission distance; communication rate; time fluctuation of the signal level of the transmission signal; time fluctuation of the signal level of the reception signal; and BER, in wireless communication between the transceivers 58 and 96. Thus, it is possible to reliably select one radiation converter and one console that have the most appropriate communication state.

In this case, the selector 85, the console retrieving unit 90 (90a to 90c), or the radiation converter retrieving unit 91 selects a radiation converter and a console that are placed in at least one communication state of: a communication state where the time-average of the signal level of the transmission signal is the largest; a communication state where the time-average of the signal level of the reception signal is the largest; a communication state where the transmission distance is the shortest; a communication state where the communication rate is the fastest; a communication state where the time-fluctuation of the signal level of the transmission signal is the smallest; a communication state where the time-fluctuation of the signal level of the reception signal is the smallest; and a communication state where the BER is the lowest, as one radiation converter and one console that have the most appropriate communication state. Thus, one radiation converter and one console can be selected accurately.

The radiation converter 38 (38a to 38c) further includes the ID memory 94 for holding the ID information for specifying the radiation converter 38 (38a to 38c). The transceiver 58 sends the ID information and the radiographic image to the outside. One console receives the ID information. If the received ID information coincides with ID information of one radiation converter indicated by the indication signal, the one console processes the radiographic image that has been received together with the ID information. Thus, the one console can process reliably the radiographic image that is sent from the associated radiation converter.

In this case, the consoles 24, 26, 28 each include the ID memory 106 for registering therein the ID information. If ID information received by one console coincides with ID information of one radiation converter registered in the ID memory 106, the one console processes the received radiographic image. Thus, when the ID information coincides with each other, one console judges that the received radiographic image has been sent from the associated radiation converter, and processes the received radiographic image. Conversely, if the ID information does not coincide with each other, the one console judges that the received radiographic image has been sent from the non-associated radiation converter, and does not process the radiographic image. As a result, a radiographic image can be processed efficiently.

Further, signals are transmitted and received by way of wireless communication between the consoles 24, 26, 28 and the transceivers 58. In other words, cables for transmitting and receiving signals are not connected between the consoles 24, 26, 28 and the radiation converters 38 (38a to 38c). Accordingly, such cables are not placed on the floors of the image-capturing rooms 18, 20, 22 where they otherwise would become obstacles to the operation performed by the radiological technician. Thus, the radiological technician can perform work more efficiently. If the above wireless communication comprises the UWB wireless communication, it is possible to reduce power consumption, increase fading resistance, and increase communication rates, compared with other wireless communications.

On the side of the console 24 (26, 28), the technician or the like can change the association of one radiation converter with one console into another association of the one radiation converter with another console, another association of another radiation converter with the one console, or another association of another radiation converter with another console. For example, when the technician brings the radiation converter 38 into the image-capturing room 18 having the console 24, but the radiation converter 38 is associated with the console 26 or 28, not with the console 24, the technician can change the association such that the radiation converter 38 is associated with the console 24 connected to the image-capturing room 18. Thus, reduction in burdens on the technician and the subject 32, reduction in the working hours required for image-capturing, and improvement in the efficiency for image-capturing are achieved simultaneously.

More specifically, in the consoles 24, 26, 28, the display units 110 display the association result of one radiation converter with one console. Based on the displayed result, the technician operates the input operating unit 108. By the operation, the association of the one radiation converter with the one console is changed easily into another association.

Also, the ordering information stored in the ordering information storage unit 100 and the image capturing conditions stored in the image capturing condition storage unit 102 are changed depending on the association of one radiation converter and one console or the changed association. Owing thereto, an image of the subject 32 can be captured correctly. Further, since the display unit 110 displays the changed association result, the technician can confirm reliably whether the input through the input operating unit 108 is reflected in the changed association result or not.

The present embodiment is not limited in the above explanations, and may be changed into the below configurations.

In the present embodiment, as described above, when a plurality of the radiation converters 38 (38a to 38c) and a plurality of the consoles 24, 26, 28 are provided, one radiation converter and one console that have the most appropriate communication state are associated with each other (see FIGS. 8A, 8B, 10B and 12B).

Where the above-explanations are extended, i.e., when a plurality of the radiation converters 38a to 38c and a plurality of the consoles 24, 26, 28 are provided, a priority order may be determined in order of good communication state between the radiation converters 38a to 38c and the consoles 24, 26, 28, and according to the determined priority order, the association process may be performed.

More specifically, the selector 85, the console retrieving unit 90a to 90c, or the radiation converter retrieving unit 91 determines the priority order of good communication states between the transceivers 58 and 96. Based on the determined priority order, the selector 85 or the above performs the association process, and then sends the association result as an indication signal to the radiation converters 38a through 38c and the consoles 24, 26, 28 of the radiographic image capturing system 10. When communication is performed between the transceivers 58, 96 based on the priority order indicated by the indication signal, if one or both of the transceivers 58 and 96 that are associated with each other based on a desired priority (for example, the highest priority) is in use, communication is performed between the transceivers 58 and 96 in a lower-priority association (for example, the next-highest-priority association).

The association process based on the priority order will be described in more detail below.

In the case where a plurality of the radiation converters 38a to 38c and a plurality of the consoles 24, 26, 28 are provided, the selector 85, the console retrieving unit 90a to 90c, or the radiation converter retrieving unit 91 associates, for example, one radiation converter 38a with the consoles 24, 26, 28 in order of good communication state.

More specifically, for example, in a case where the communication state between the radiation converter 38a and the console 24 is the best, the communication state between the radiation converter 38a and the console 26 is the second best, and the communication state between the radiation converter 38a and the console 28 is relatively bad, the selector 85, the console retrieving unit 90a to 90c, or the radiation converter retrieving unit 91 determines the priority order of the above good communication states (i.e., the first is the association of the radiation converter 38a and the console 24, the second is the association of the radiation converter 38a and the console 26, and the third is the association of the radiation converter 38a and the console 28).

Based on the determined priority order, the selector 85, the console retrieving unit 90a to 90c, or the radiation converter retrieving unit 91 associates the radiation converter 38a with the console 24, the radiation converter 38a with the console 26, and the radiation converter 38a with the console 28, and generates an indication signal representing the above association result. According to the priority order, the radiation converter 38a communicates with the console 24, which provides the best communication state.

The association process (determination of the priority order) of the radiation converter 38b and the consoles 24, 26, 28, the association process of the radiation converter 38c and the consoles 24, 26, 28, the association process of the console 24 and the radiation converters 38a to 38c, the association process of the console 26 and the radiation converters 38a to 38c, and the association process of the console 28 and the radiation converters 38a to 38c are performed similarly. The communication state, which is the basis for determining the priority order, can be confirmed by checking the magnitude of the signal level of the reception signal, the transmission distance between the transceivers 58 and 96, the communication rate between the transceivers 58 and 96, and the bit error rate (BER).

As described above, the selector 85, the console retrieving unit 90a to 90c, or the radiation converter retrieving unit 91 determines the priority order of good communication states between the radiation converters 38a to 38c and the consoles 24, 26, 28, and then performs the association process based on the determined priority order. Accordingly, the technician does not need to perform the association process, and the association process can be performed efficiently.

Also, since the association process is performed based on the priority order of good communication states, the good communication state between the radiation converters 38a to 38c and the consoles 24, 26, 28 is ensured, and thus radiographic images can be transmitted/received stably.

Next, explanations will be made in the case where when one transceiver 58 or 96 in the desired association is busy, a transceiver 58 or 96 in a lower priority association is used for communication instead of the one transceiver 58 or 96 in the desired association.

For example, the following case is considered. That is, in the priority order of the associations of the radiation converter 38a and the consoles 24, 26, 28, the first is the association of the radiation converter 38a with the console 24, the second is the association of the radiation converter 38a with the console 26, and the third is the association of the radiation converter 38a with the console 28; and in the priority order of the associations of the radiation converter 38b and the consoles 24, 26, 28, the first is the association of the radiation converter 38b with the console 24, the second is the association of the radiation converter 38b with the console 26, and the third is the association of the radiation converter 38b with the console 28. In this case, the consoles that provide the highest priority associations (the best communication states) with the radiation converters 38a, 38b are both the console 24.

In the above case, when the console 24 is busy communicating with the radiation converter 38a, if the radiation converter 38b communicates with the console 24, which provides the highest priority association with the radiation converter 38b, the communication rate between the radiation converter 38a and the console 24 may become lower. In such a state, if the radiation converter 38b communicates with the console 24, an expected communication rate may not be obtained between the radiation converter 38b and the console 24. As such, the radiation converter 38b stops communication with the console 24, and then communicates with the console 26, which provides the next highest priority association.

Thus, when the selector 85, the console retrieving unit 90a to 90c, or the radiation converter retrieving unit 91 previously sends an indication signal indicating the priority order of the associations to the radiation converters 38a to 38c and the consoles 24, 26, 28, each of the radiation converters 38a to 38c and the consoles 24, 26, 28 can select, according to the priority order, a counterpart that provides the highest communication rate in the current situation, in view of the communication states of the existing communications, i.e., without impairing the communication states of the existing communications. Thus, radiographic images and the like can be transmitted/received more stably.

In the above explanation, the radiation converters 38a, 38b communicate with the consoles 24, 26, as viewed from the radiation converters 38a, 38b. However, the present invention is not limited to this case, and may be similarly applied to another cases where another radiation converters communicate with another consoles.

Also, in the embodiments of the present invention, the radiation converters 38 and the consoles 24, 26, 28 may transmit/receive signals therebetween by wired communication, instead of wireless communication. In this case also, the above advantageous effects by the association process in which the selected one console is associated with the radiation converter 38 can be obtained.

Also, in the present embodiments, the explanations have been made in the case where the transceivers 58, 96 are used as a short-range radar by UWB, or as a position detection mechanism using a wireless LAN. However, a UWB short-range radar having the above functions or a wireless LAN position detection mechanism having the above functions may be provided separately from the transceivers 58, 96, and then the above effects can be also obtained easily. Further, the selector 85 may include, for example, a spectrum analyzer which sweeps the reception signal in the frequency direction and measures its signal level accurately. In this case, one radiation converter and/or one console can be selected more correctly.

Further, the present invention is not limited to use in the image-capturing rooms 18, 20, 22, but may be used in an operation in the operating room, medical examinations or used by doctors when going the rounds in hospitals, for example.

Still further, the radiation converters 38 and the consoles 24, 26, 28 may transmit/receive signals therebetween by optical wireless communication such as infrared communication. In this case, the above effects can be also obtained easily.

The radiation converter 38 may comprise a indirect-conversion type radiation converter including a scintillator for converting the applied radiation 36 into visible light and a solid-state detecting device such as of amorphous silicon (a-Si) or the like for converting the visible light into an electric signal (see Japanese Patent No. 3494683).

Alternatively, the radiation converter 38 may employ a light-readout type radiation conversion panel for acquiring a radiographic image. The light-readout type radiation conversion panel operates as follows: When radiation 36 is applied to a matrix of solid-state detecting devices, the solid-state detecting devices store an electrostatic latent image depending on the dose of the applied radiation. For reading the stored electrostatic latent image, reading light is applied to the radiation conversion panel, and the generated electric current values are acquired as a radiographic image. When erasing light is applied to the radiation conversion panel, a radiographic image representing a residual electrostatic latent image is erased from the radiation conversion panel, which can thus be reused (see Japanese Laid-Open Patent Publication No. 2000-105297).

Although certain preferred embodiments of the present invention have been shown and described in detail, it should be understood that various changes and modifications may be made therein without departing from the scope of the appended claims.

What is claimed is:

1. A radiographic image capturing system comprising:
   a plurality of radiation converters and one processor, one radiation converter and a plurality of processors, or a plurality of radiation converters and a plurality of processors, wherein each radiation converter converts radiation that has passed through a subject into a radiographic image, and each processor processes the radiographic image; and
   a selector for selecting one radiation converter and one processor based on a communication state between each radiation converter and each processor, and associating the selected one radiation converter with the selected one processor.

2. A radiographic image capturing system according to claim 1, wherein the each radiation converter includes a first communication unit for communicating with an external device,
   the each processor includes a second communication unit for communicating with an external device, and the selector selects the one radiation converter and the one processor based on a communication state between the first communication unit and the second communication unit, and sends, as an indication signal, an association result that the selected one radiation converter and the selected one processor have been associated with each other, to the radiation converters and the processors in the radiographic image capturing system.

3. A radiographic image capturing system according to claim 2, wherein the selector selects the one radiation converter and the one processor based on at least one of transmission intensity, reception intensity, transmission distance, communication rate, time-fluctuation of the transmission intensity, time-fluctuation of the reception intensity, and bit error rate, in communication between the first communication units and the second communication units.

4. A radiographic image capturing system according to claim 3, wherein the selector selects the one radiation converter and the one processor that are placed in at least one of the following communication states: a communication state in which a time-average of the transmission intensity is the largest; a communication state in which a time-average of the reception intensity is the largest; a communication state in which the transmission distance is the shortest; a communication state in which the communication rate is the fastest; a communication state in which the time-fluctuation of the transmission intensity is the smallest; a communication state in which the time-fluctuation of the reception intensity is the smallest; and a communication state in which the bit error rate is the lowest.

5. A radiographic image capturing system according to claim 2, wherein the each radiation converter further includes an identification information holding unit for holding identification information for specifying the radiation converter,
the first communication unit sends the identification information and the radiographic image to an external device, and
the one processor receives the sent identification information, and if the received identification information represents the one radiation converter indicated by the indication signal, the one processor processes the radiographic image that has been received together with the identification information.

6. A radiographic image capturing system according to claim 5, wherein the each processor further include an identification information registration unit for registering the identification information, and
if the received identification information coincides with identification information representing the one radiation converter, which is registered in the identification information registration unit, the one processor processes the radiographic image.

7. A radiographic image capturing system according to claim 2, wherein the first communication unit and the second communication unit each include a wireless transceiver for sending/receiving a signal by wireless communication.

8. A radiographic image capturing system according to claim 2, wherein when a plurality of the processors and one radiation converter are provided, the selector serves as a processor selector for comparing the communication states between the second communication units of the processors and the first communication unit of the one radiation converter, selecting the one processor based on a communication state with the one radiation converter from among the processors, associating the selected one processor with the one radiation converter, and sending the association result as the indication signal, to the one radiation converter and the processors.

9. A radiographic image capturing system according to claim 8, wherein the one radiation converter has the processor selector,
the processor selector outputs the indication signal to the first communication unit of the one radiation converter, and
the first communication unit sends the indication signal to the second communication unit of each processor.

10. A radiographic image capturing system according to claim 2, wherein when a plurality of the radiation converters and one processor are provided, the selector serves as a radiation converter selector for comparing the communication states between the first communication units of the radiation converters and the second communication unit 96 of the one processor, selecting the one radiation converter based on a communication state with the one processor from among the radiation converters, associating the selected one radiation converter with the one processor, and sending the association result as the indication signal, to the one processor and the radiation converters.

11. A radiographic image capturing system according to claim 10, wherein the one processor has the radiation converter selector,
the radiation converter selector outputs the indication signal to the second communication unit of the one processor, and
the second communication unit sends the indication signal to the first communication unit of each radiation converter.

12. A radiographic image capturing system according to claim 2, wherein when a plurality of the radiation converters and a plurality of the processors are provided, the selector compares the communication states between the first communication units of the radiation converters and the second communication units of the processors, selects at least one pair of the one radiation converter and one processor based on a communication state, associates the selected one radiation converter with the selected one processor, and sends the association result as the indication signal to the radiation converters and the processors.

13. A radiographic image capturing system according to claim 1, further comprising a changer for changing the association of the one radiation converter with the one processor by the selector into an association of the one radiation converter with another processor, an association of another radiation converter with the one processor, or an association of another radiation converter with another processor.

14. A radiographic image capturing system according to claim 13, wherein the changer comprises:
an output unit for outputting the association result by the selector to an external device; and
an input operating unit for performing an input operation to change the association by the selector based on an output result from the output unit.

15. A radiographic image capturing system according to claim 14, wherein the processors each include the changer, a controller, an ordering information registration unit for registering ordering information for capturing an image of the subject, the ordering information including a given image capturing condition, and an image capturing condition registration unit for registering the image capturing condition,
the controller changes the ordering information registered in the ordering information registration unit and the image capturing condition registered in the image capturing condition registration unit based on the association result by the selector or based on the change of the association by the changer, and the output unit comprises a display unit for displaying the association result by the selector or the change of the association by the changer.

16. A radiographic image capturing system according to claim 1, further comprising a radiation source, the radiation source being controlled based on a given image capturing condition to apply the radiation to the subject.

17. A radiographic image capturing system comprising:
a plurality of radiation converters for converting radiation that has passed through a subject into a radiographic image;
a plurality of processors for processing the radiographic image; and
a selector for determining a priority order for communication based on communication states between the radiation converters and the processors, and associating the radiation converters with the processors based on the determined priority order.

18. A radiographic image capturing system according to claim 17, wherein the radiation converters each include a first communication unit for communicating with an external device,
the processors each include a second communication unit for communicating with an external device, and
the selector determines a priority order for communication based on communication states between the first communication units and the second communication units, associates the first communication units with the second communication units based on the determined priority order, and sends the association result as an indication signal to the radiation converters and the processors in the radiographic image capturing system.

19. A radiographic image capturing system according to claim 18, wherein when communication between the first communication units and the second communication units is performed based on the priority order indicated by the indication signal, if the first communication unit or the second communication unit in a desired priority association selected according to the priority order is in use, another first communication unit or another second communication unit in a lower-priority association is used for communication.

20. A radiation converter for converting radiation that has passed through a subject into a radiographic image, the radiation converter comprising a selector, wherein when a plurality of processors for processing the radiographic image are provided, the selector selects one processor based on a communication state, from among the processors, and associates the selected one processor with the radiation converter.

21. A radiation converter for converting radiation that has passed through a subject into a radiographic image, the radiation converter comprising a selector, wherein a plurality of the radiation converters and a plurality of processors for processing the radiographic image are provided, the selector determines a priority order for communication based on communication states between the radiation converters and the processors, and associates the radiation converters with the processors based on the determined priority order.

22. A processor for processing a radiographic image, the processor comprising a selector, wherein when a plurality of radiation converters for converting radiation that has passed through a subject into the radiographic image are provided, the selector selects one radiation converter based on a communication state, from among the radiation converters, and associates the selected one radiation converter with the processor.

23. A processor for processing a radiographic image, the processor comprising a selector, wherein when a plurality of the processors and a plurality of radiation converters for converting radiation that has passed through a subject into the radiographic image are provided, the selector determines a priority order for communication based on communication states between the radiation converters and the processors, and associates the radiation converters with the processors based on the determined priority order.

24. A selector for selecting a radiation converter and a processor, the radiation converter converting radiation that has passed through a subject into a radiographic image, the processor for processing the radiographic image, wherein when at least a plurality of the radiation converters or a plurality of the processors are provided, the selector selects one radiation converter and one processor based on a communication state, and associates the selected one radiation converter with the selected one processor.

25. A selector for selecting a radiation converter and a processor, the radiation converter converting radiation that has passed through a subject into a radiographic image, the processor for processing the radiographic image, wherein when a plurality of the radiation converters and a plurality of the processors are provided, the selector determines a priority order for communication based on communication states between the radiation converters and the processors, and associates the processors with the processors based on the determined priority order.

26. A non-transitory computer readable medium storing a program for being executed by a selector when at least a plurality of radiation converters or a plurality of processors are provided, the radiation converters converting radiation that has passed through a subject into a radiographic image, the processors for processing the radiographic image, the program comprising the steps of:
selecting one radiation converter and one processor based on a communication state; and
associating the selected one radiation converter with the selected one processor.

27. A non-transitory computer readable medium storing a program for being executed by a selector when a plurality of radiation converters and a plurality of processors are provided, the radiation converters converting radiation that has passed through a subject into a radiographic image, the processors for processing the radiographic image, the program comprising the steps of:
determining a priority order for communication based on communication states between the radiation converters and the processors; and
associating the radiation converters with the processors based on the determined priority order.

28. A method of selecting a radiation converter a processor, the radiation converter converting radiation that has passed through a subject into a radiographic image, the processor for processing the radiographic image, at least a plurality of the radiation converters or a plurality of the processors being provided, the method comprising the steps of:
selecting one radiation converter and one processor based on a communication state; and
associating the selected one radiation converter with the selected one processor.

29. A method of selecting a radiation converter a processor, the radiation converter converting radiation that has passed through a subject into a radiographic image, the processor for processing the radiographic image, a plurality of the radiation converters and a plurality of the processors being provided, the method comprising the steps of:

determining a priority order for communication based on a communication state between the radiation converters and the processors; and associating the radiation converters with the processors based on the determined priority order.

30. A radiographic image capturing method, at least a plurality of radiation converters or a plurality of processors being provided, the method comprising the steps of:

selecting one radiation converter and one processor based on a communication state;

associating the selected one radiation converter with the selected one processor;

converting radiation that has passed through a subject into a radiographic image with the selected one radiation converter;

sending the converted radiographic image to the one processor; and processing the radiographic image with the one processor.

31. A radiographic image capturing method, a plurality of radiation converters and a plurality of processors being provided, the method comprising the steps of:

determining a priority order for communication based on communication states between the radiation converters with the processors;

associating the radiation converters with the processors based on the determined priority order;

converting radiation that has passed through a subject into a radiographic image with the associated one radiation converter;

sending the converted radiographic image to the associated one processor; and processing the radiographic image with the one processor.

\* \* \* \* \*